US010357518B2

(12) United States Patent
Bravo et al.

(10) Patent No.: US 10,357,518 B2
(45) Date of Patent: Jul. 23, 2019

(54) ADIPOSE TISSUE-DERIVED STROMAL STEM CELLS FOR USE IN TREATING REFRACTORY COMPLEX PERIANAL FISTULAS IN CROHN'S DISEASE

(71) Applicant: TIGENIX S.A.U., Madrid (ES)

(72) Inventors: Eduardo Bravo, Madrid (ES); Maria Pascual, Madrid (ES)

(73) Assignee: TIGENIX S.A.U., Madrid (ES)

(*) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 15/458,509

(22) Filed: Mar. 14, 2017

(65) Prior Publication Data
US 2017/0258851 A1  Sep. 14, 2017

(30) Foreign Application Priority Data

Mar. 14, 2016  (GB) .................. 1604304.4

(51) Int. Cl.
*A61K 35/35* (2015.01)
*A61K 35/28* (2015.01)

(52) U.S. Cl.
CPC .............. *A61K 35/35* (2013.01); *A61K 35/28* (2013.01)

(58) Field of Classification Search
CPC ..... A61K 35/35; A61K 35/28; A61L 27/3604; A61L 27/3834; A61L 27/3839
See application file for complete search history.

(56) References Cited

U.S. PATENT DOCUMENTS

| | | |
|---|---|---|
| 5,578,475 A | 11/1996 | Jessee |
| 5,627,175 A | 5/1997 | Simon |
| 5,705,308 A | 1/1998 | West et al. |
| 5,744,335 A | 4/1998 | Wolff et al. |
| 5,855,619 A | 1/1999 | Caplan et al. |
| 5,976,567 A | 11/1999 | Wheeler et al. |
| 6,020,202 A | 2/2000 | Jessee |
| 6,051,429 A | 4/2000 | Hawley-Nelson et al. |
| 6,174,333 B1 | 1/2001 | Kadiyala et al. |
| 6,555,374 B1 | 4/2003 | Gimble et al. |
| 6,777,231 B1 | 8/2004 | Katz et al. |
| 7,645,229 B2 | 1/2010 | Armstrong |
| 7,732,126 B2 | 6/2010 | Zhang et al. |
| 8,999,709 B2 | 4/2015 | Fernández Miguel et al. |
| 2003/0082152 A1 | 5/2003 | Hedrick et al. |
| 2004/0180040 A1 | 9/2004 | Phillips et al. |
| 2005/0048644 A1 | 3/2005 | Hedrick et al. |
| 2005/0054098 A1 | 3/2005 | Mistry et al. |
| 2005/0153442 A1 | 7/2005 | Katz et al. |
| 2005/0239897 A1 | 10/2005 | Pittenger et al. |
| 2006/0045872 A1 | 3/2006 | Miguel et al. |
| 2006/0047312 A1 | 3/2006 | Garcia Olmo et al. |
| 2006/0073124 A1 | 4/2006 | Garcia Castro et al. |
| 2007/0178071 A1 | 8/2007 | Westenfelder et al. |
| 2008/0095749 A1 | 4/2008 | Aggarwal et al. |
| 2010/0098669 A1 | 4/2010 | Fernández Miguel et al. |
| 2010/0209403 A1 | 8/2010 | Meiron et al. |
| 2011/0262402 A1 | 10/2011 | Kuroda et al. |
| 2012/0020937 A1 | 1/2012 | Lee et al. |
| 2012/0269774 A1 | 10/2012 | Ichim et al. |
| 2014/0072539 A1 | 3/2014 | Miguel et al. |
| 2014/0134140 A1 | 5/2014 | Caplan et al. |
| 2015/0065948 A1* | 3/2015 | Fernández Miguel ..................... A61L 24/106 604/22 |

FOREIGN PATENT DOCUMENTS

| | | |
|---|---|---|
| WO | WO-02067867 A2 | 9/2002 |
| WO | WO-03022988 A2 | 3/2003 |
| WO | WO-03024215 A1 | 3/2003 |
| WO | WO-2005035738 A1 | 4/2005 |
| WO | WO-2005042730 A2 | 5/2005 |
| WO | WO-2005093044 A1 | 10/2005 |
| WO | WO-2006037649 A1 | 4/2006 |
| WO | WO-2006136244 A2 | 12/2006 |
| WO | WO-2008036374 A2 | 3/2008 |
| WO | WO-2008116157 A2 | 9/2008 |
| WO | WO-2009050282 A1 | 4/2009 |
| WO | WO 2010/112662 A1 | 10/2010 |
| WO | WO-2012095743 A2 | 7/2012 |
| WO | WO-2012123401 A1 | 9/2012 |
| WO | WO 2014/140362 A2 | 9/2014 |
| WO | WO-2014207679 A1 | 12/2014 |

OTHER PUBLICATIONS

Portilla et al., Expanded allogeneic adipose-derived stem cells (eASCs) for the treatment of complex perianal fistula in Crohn's disease: results from a multicenter phase I/IIa clinical trial. International Journal of Colorectal Disease, vol. 28, No. 3 (Mar. 2013) pp. 313-323.*
Abkowitz, Janis L., "Can Human Hematopoietic Stem Cells Become Skin, Gut, or Liver Cells?", The New England Journal of Medicine, vol. 346, No. 10, Mar. 7, 2002, pp. 770-772.
Anonymous (2013). "TiGenix Press Release 2013," Available at URL: http://www.tigenix.comjenjpages/11/2013, 2 pages.
Anonymous (2015). "Cx601 (Alofisel) for complex perianal fistula in adults with non-active or mildly-active luminal Chron's disease—second line," National Institute for Health Research Horizon Scanning Centre, 8 pages.
Anonymous (2015). "TiGenix announces Cx601 meets primary endpoint in pivotal Phase III trial," TiGenix press release, 4 pages.
Anonymous (2016). "TiGenix announces positive 52-week Phase III results of Cx601 in complex perianal fistulas in Crohn's disease patients," TiGenix press release, 3 pages.
Anonymous, "American Gastroenterological Association Medical Position Statement: Perianal Crohn's Disease", Gastroenterology, vol. 125, No. 5, Nov. 2003, pp. 1503-1507.
Anonymous, "Cx611 in RA", available online at <http://www.tigenix.com/en/download/?s=rNXU8lvo7ZUjEybwArESBX4S%2BkEKDIBvQYuoUTu%2FQzzXtBQzMAI7TEC318DkwthFj%2BYyaSGvZW9cSU6K1 0OQDQ%3D%3D>, 2013, By TiGenix, 47 pages.

(Continued)

Primary Examiner — Satyendra K Singh
(74) Attorney, Agent, or Firm — Morrison & Foerster LLP

(57) ABSTRACT

Provided herein are expanded allogeneic adipose tissue-derived stromal stem cells for use in treating complex perianal fistulas in Crohn's Disease.

20 Claims, 4 Drawing Sheets

(56) References Cited

OTHER PUBLICATIONS

Anonymous, "Isolation, Propagation and Characterization of Human Mesenchymal Stem Cells", Final Report N-01191, Vivotecnia Research S.L., Mar. 23, 2011, 47 pages.
Anonymous, "TiGenix Completes EUR 6.5 million Capital Increase", available online at <http://www.tigenix.com/en/download/?s=Z26Ua20y8Za%2FoG0QmRK8XeAKmi8idp%2FrsRyPi2HQV9vBBMGzfBT6aFG%2FibaP7g55QAMhyS0qtkaBEjVvEBPcAg%3D%3D>, Jul. 26, 2013, By TiGenix, pp. 1-2.
Anonymous, "TiGenix Reports Positive Phase IIa Study Results in Refractory Rheumatoid Arthritis with Allogeneic Stem Cell Product Cx611 ", retrieved from <http://www.tigenix.com/public/uploads/pdf/en/f5177d809eca202.40307502_TiGenix%20Cx611%20Phase%20IIa%20results%20Final.pdf, Apr. 22, 2013, by TiGenix, 3 pages.
Astori, et al., "In Vitro' and Multicolor Phenotypic Characterization of Cell Subpopulations Identified in Fresh Human Adipose Tissue Stromal Vascular Fraction and in the Derived Mesenchymal Stem Cells", Journal of Translational Medicine, vol. 5, 2007, pp. 1-10.
Awad et al., "Chondrogenic Differentiation of Adipose-Derived Adult Stem Cells Agarose, Alginate, and Gelatin Scaffolds", Biomaterials, vol. 25, No. 16, 2004, pp. 3211-3222.
Barry, et al., "Mesenchymal Stem Cells: Clinical Applications and Biological Characterization", Int. J. Biochem. Cell Biol, vol. 36, No. 4, 2004, pp. 568-584.
Baumgart et al. (2012). "Crohn's disease," Lancet. 380(9853):1590-605.
Bell et al. (2003). "The clinical course of fistulating Crohn's disease," Aliment Pharmacol Ther. 17(9):1145-51.
Beresford et al., "Evidence for an Inverse Relationship Between the Differentiation of Adipocytic and Osteogenic Cells in Rat Marrow Stromel Cell Cultures", Journal of Cell Science, vol. 102, 1992, pp. 341-351.
Best et al. (1976). "Development of a Crohn's disease activity index. National Cooperative Crohn's Disease Study," Gastroenterology. 70(3):439-44.
Bochev et al., "Mesenchymal stem cells from human bone marrow or adipose tissue differently modulate mitogen-stimulated B-cell immunoglobulin production in vitro", Cell Biology International, 2008, vol. 32, 384-393.
Bourin et al., "Stromal Cells from the Adipose Tissue-derived Stromal Vascular Fraction and Culture Expanded Adipose Tissue-derived Stromal/stem Cells: A Joint Statement of The International Federation for Adipose Therapeutics and Science (IFATS) and The International Society for Cellular Therapy (ISCT)", Cytotherapy, vol. 15, No. 6, Jun. 1, 2013, pp. 641-648.
Brady et al., "Closure of a Duodenal Fistula with Fibrin Sealant", Journal of Vascular and Interventional Radiology, vol. 4, No. 4, 1993, pp. 525-529.
Brandt et al. (1982). "Metronidazole therapy for perineal Crohn's disease: a follow-up study," Gastroenterology. 83(2):383-7.
Byk, Tamara, et al., "Lipofectamine and Related Cationic Lipids Strongly Improve Adenoviral Infection Efficiency of Primitive Human Hematopoietic Cells," Human Gene Therapy, 1998, pp. 2493-2502, vol. 9.
Cai et al., "Adipose Stem Cells Originate from Perivascular Cells", Biol. Cell, vol. 103, No. 9, 2011, pp. 435-447.
Cao et al., "Human Adipose Tissue-Derived Stem Cells Differentiate Into Endothelial Cells in Vitro and Improve Postnatal Neovascularization in Vivo", Biochem. and Biophys. Res. Comm., vol. 332, No. 2, 2005, pp. 370-379.
Caplan A. I., "Mesenchymal Stem Cells: Cell-Based Reconstructive Therapy in Orthopedics", Tiss. Eng., vol. 11, No. (7-8), 2005, pp. 1198-1211.
Caplan et al., "Mesenchymal Stem Cells: Building Blocks for Molecular Medicine in the 21st Century", Trends in Molecular Medicine, vol. 7, No. 6, Jun. 2001, pp. 259-264.
Caplan, Arnold I., "Mesenchymal Stem Cells", Journal of Orthopedic Research, vol. 9, No. 5, 1991, pp. 641-650.

Chandra et al., "Generation of Pancreatic Hormone-Expressing Islet-Like Cell Aggregates from Murine Adipose Tissue-Derived Stem Cells", Stem Cells, vol. 27, 2009, pp. 1941-1953.
Cho et al. (2015). "Long-term results of adipose-derived stem cell therapy for the treatment of Crohn's fistula," Stem Cells Transl Med., 4(5):532-7.
Colombel et al. (2009). "Adalimumab for the treatment of fistulas in patients with Crohn's disease," Gut. 58(7):940-8.
Committee for Advanced Therapies, "Reflection Paper on Stem Cell-Based Medicinal Products", European Medicines Agency, EMA/CAT/571134/2009, Jan. 14, 2011, 14 pages.
Cowan et al., "Adipose-Derived Adult Stromal Cells Heal Critical-Size Mouse Calvarial Defects", Nature Biotechnology, vol. 22, No. 5, May 2004, pp. 560-567.
Crisan et al., "A Perivascular Origin for Mesenchymal Stem Cells in Multiple Human Organs", Cell Stem Cell, vol. 3, No. 3, 2008, pp. 301-313.
Zuk et al., "Multilineage Cells from Human Adipose Tissue: Implications for Cell-Based Therapies", Tissue Engineering, vol. 7, No. 2, 2001, pp. 211-228.
De Ugarte et al., "Comparison of Multi-Lineage Cells from Human Adipose Tissue and Bone Marrow", Cells Tissues Organs, vol. 174, 2003, pp. 101-109.
Declaration by Dr. Mario Delgado dated Mar. 26, 2011, submitted in U.S. Appl. No. 95/001,592, 27 pages.
Declaration by Dr. Mario Delgado dated Sep. 30, 2011, submitted in U.S. Appl. No. 95/001,592, 27 pages.
Declaration of Farshid Guilak Pursuant to 37 CFR § 1.132, filed Aug. 31, 2011, 19 pages.
DelaRosa et al. (2009). "Requirement of IFN-gamma-mediated indoleamine 2,3-dioxygenase expression in the modulation of lymphocyte proliferation by human adipose-derived stem cells," Tissue Eng Part A. 15(10):2795-806.
Delarosa, "Mesenchymal Stem Cells as Therapeutic Agents of Inflammatory and Autoimmune Diseases", Current Opinion in Biotechnology, vol. 23, Jun. 2012, No. 6, pp. 978-983.
Domenech et al. (2005). "Clinical evolution of luminal and perianal Crohn's disease after inducing remission with infliximab: how long should patients be treated?" Aliment Pharmacol Ther, 22:1107-13.
Eglinton et al. (2012). "The spectrum of perianal Crohn's disease in a population-based cohort," Dis Colon Rectum. 55(7):773-7.
Entenmann et al., "Relationship between Replication and Differentiation in Cultured Human Adipocyte Precursor Cells", Am. J. Physiol., vol. 270 (4 Pt 1), 1996, pp. C1011-C1016.
Estes et al., "Monolayer Cell Expansion Conditions Affect the Chondrogenic Potential of Adipose-Derived Stem Cells", Biotechnology and Bioengineering, vol. 99, No. 4, Mar. 1, 2008, pp. 986-995.
Final Office Action received for U.S. Appl. No. 11/167,061, dated Oct. 26, 2011, 8 pages.
Final Office Action received for U.S. Appl. No. 11/993,859, dated Nov. 25, 2013, 29 pages.
Final Office Action received for U.S. Appl. No. 14/017,152, dated Mar. 6, 2017, 12 pages.
Final Office Action received for U.S. Appl. No. 14/017,152, dated Oct. 7, 2015, 7 pages.
Friedenstein et al., "Fibroblast Precursors in Normal and Irradiated Mouse Hematopoietic Organs", Exp. Hemat., vol. 4, 1976, pp. 267-274.
Garcia-Olmo et al. (2015). "Cumulative Evidence That Mesenchymal Stem Cells Promote Healing of Perianal Fistulas of Patients With Crohn's Disease—Going From Bench to Bedside," American Gastroenterological Association Institute, vol. 149, Issue 4, pp. 853-857.
Garcia-Olmo et al. (2015). "Recurrent anal fistulae: limited surgery supported by stem cells," World J Gastroenterol. 21:3330-6.
Garcia-Olmo et al., "A Phase I Clinical Trial of the Treatment of Crohn's Fistula by Adipose Mesenchymal Stem Cell Transplantation", Diseases of the Colon and Rectum, vol. 48, No. 7, Jul. 2005, pp. 1416-1423.

(56) References Cited

OTHER PUBLICATIONS

Garcia-Olmo et al., "Autologous Stem Cell Transplantation for Treatment of Rectovaginal Fistula in Perianal Crohn's Disease: A New Cell-Based Therapy", Int. J. Colorectal Dis., vol. 18, 2003, pp. 451-454.
Garcia-Olmo et al., "The Vulture and Stem Cells", The New England Journal of Medicine, vol. 349, No. 15, Oct. 9, 2003, pp. 1480-1481.
Gecse et al. (2013). "Fistulizing Crohn's disease: Diagnosis and management," United European Gastroenterol J, 1:206-13.
Geltzeiler et al. (2014). "Recent developments in the surgical management of perianal fistula for Crohn's disease," Ann Gastroenterol 2014;27:320-30.
Gimble et al., "Differentiation Potential of Adipose Derived Adult Stem (ADAS) Cells", Curr. Top Dev. Biol., vol. 58, 2003, pp. 137-160.
Gimble et al., "Isolation and Growth of Stem Cells", Chapter 6 in Tissue Engineering, 2011, pp. 93-111.
Gimble J.M., "Adipose Tissue-Derived Therapeutics", Exp. Op. Biol. Ther., vol. 3, No. 5, 2003, pp. 705-713.
Goldstein et al. (2004). "6-Mercaptopurine is effective in Crohn's disease without concomitant steroids," Inflamm Bowel Dis. 10(2):79-84.
Gomillion, et al., "Stem Cells and Adipose Tissue Engineering", Biomaterials, vol. 27, 2006, pp. 6052-6063.
Gonzalez-Rey et al., "Human Adipose-derived Mesenchymal Stem Cells reduce Inflammatory and T Cell Responses and Induce Regulatory T Cells in Vitro in Rheumatoid Arthritis", Annals of the Rheumatic Diseases, vol. 69, Jan. 2010, No. 1, pp. 241-248.
Guadalajara et al. (2016). "Prospect of Cell Therapy for Treating Perianal Fistula, Including Crohn's Disease," Int J Stem Cell Res Ther, vol. 3, Issue 1, pp. 028, 7pages.
Guilak et al., "Clonal Analysis of the Differentiation Potential of Human Adipose-Derived Adult Stem Cells", Journal of Cellular Physiology, vol. 206, No. 1, Jan. 2006, pp. 229-237.
Guyatt et al. (1989). "A new measure of health status for clinical trials in inflammatory bowel disease," Gastroenterology. 96(3):804-10.
Halme et al., "FDA Regulation of Stem-Cell-Based Therapies", NEJM, vol. 355, No. 16, 2006, pp. 1730-1735.
Hauner et al., "Promoting Effect of Glucocorticoids on the Differentiation of Human Adipocyte Precursor Cells Cultured in a Chemically Defined Medium", J. Clin. Invest., vol. 84, 1989, pp. 1663-1670.
Haynesworth et al., "Characterization of Cells with Osteogenic Potential from Human Marrow", Bone, vol. 13, 1992, pp. 81-88.
Hellers et al. (1980). "Occurrence and outcome after primary treatment of anal fistulae in Crohn's disease," Gut. 21(6):525-7.
Herreros et al., "Autologous Expanded Adipose-Derived Stem Cells for the Treatment of Complex Cryptoglandular Perianal Fistulas: a Phase III Randomized Clinical Trial (FATT 1: Fistula Advanced Therapy Trial 1) and Long-Term Evaluation", Diseases of the Colon & Rectum, vol. 55, No. 7, Jul. 2012, pp. 762-772.
Ichim et al., "Autologous Stromal Vascular Fraction Cells: A Tool for Facilitating Tolerance in Rheumatic Disease", Cellular Immunology, vol. 264, No. 1, Apr. 2010, pp. 7-17.
Ikegame et al., "Comparison of Mesenchymal Stem Cells from Adipose Tissue and Bone Marrow for Ischemic Stroke Therapy", Cytotherapy, vol. 13, No. 6, 2011, pp. 675-685.
Irvine (1995). "Usual therapy improves perianal Crohn's disease as measured by a new disease activity index. McMaster IBD Study Group," J Clin Gastroenterol, 20:27-32.
Ishimura et al., "Differentiation of Adipose-derived Stromal Vascular Fraction Culture Cells into Chondrocytes Using the Method of Cell Sorting with a Mesenchymal Stem Cell Marker", Tohoku J. Exp. Med., vol. 216, 2008, pp. 149-156.
Ivanova et al., "A Stem Cell Molecular Signature", Science, vol. 298, Oct. 18, 2002, pp. 601-604.
Ivanova-Todorova, E. "Adipose tissue-derived mesenchymal stem cells are more potent suppressors of dendritic cells differentiation compared to bone marrow-derived mesenchymal stem cells." Immunology Letters, 2009, vol. 126, pp. 37-42.
Jiang et al., "Multipotent Progenitor Cells can be Isolated from Postnatal Murine Bone Marrow, Muscle, and Brain", Experimental Hematology, vol. 30, 2002, pp. 896-904.
Kan, I., et al., Integral Therapeutic Potential of Bone Marrow Mesenchymal Stem Cells, Current Drug Targets, 2005, pp. 31-41, vol. 6.
Kern et al., "Comparative Analysis of Mesenchymal Stem Cells from Bone Marrow, Umbilical Cord Blood, or Adipose Tissue", Stem Cells, vol. 24, 2006, pp. 1294-1301.
Kim et al., "Direct Comparison of Human Mesenchymal Stem Cells Derived From Adipose Tissues and Bone Marrow in Mediating Neovascularization in Response to Vascular Ischemia", Cell Physiol. Biochem., vol. 20, 2007, pp. 867-876.
Kim et al., "Paradoxical Effects of Human Adipose Tissue-Derived Mesenchymal Stem Cells on Progression of Experimental Arthritis in SKG Mice", Cellular Immunology, vol. 292, Nov. 2014, pp. 94-101.
Kim, Jeong-Min, et al., "Systemic transplantation of human adipose stem cells attenuated cerebral inflammation and degeneration in a hemorrhagic stroke model," Brain Research, 2007, pp. 43-50, vol. 1183.
Korelitz et al. (1985). "Favorable effect of 6-mercaptopurine on fistulae of Crohn's disease," Dig Dis Sci. 30(1):58-64.
Krasnodembskaya et al., "Antibacterial Effect of Human Mesenchymal Stem Cells is Mediated in Part from Secretion of the Antimicrobial Peptide LL-37", Stem Cells, vol. 28, No. 12, Dec. 2010, pp. 2229-2238.
Kurtia et al., "Influences of Centrifugation on Cells and Tissues in Liposuction Aspirates: Optimized Centrifugation for Lipotransfer and Cell Isolation", Plast. Reconstr. Surg., vol. 121, No. 3, 2008, pp. 1033-1041.
Le Blanc et al., "Immunobiology of Human Mesenchymal Stem Cells and Future Use in Hematopoietic Stem Cell Transplantation", Biology of Blood and Marrow Transplantation, vol. 11, No. 5, May 2005, pp. 321-334.
Le Blanc, K. et al., "Immunomodulation by mesenchymal stem cells and clinical experience," Journal of Internal Medicine, 2007, pp. 509-525, vol. 262.
Lee et al., "Characterization and Expression Analysis of Mesenchymal Stem Cells from Human Bone Marrow and Adipose Tissue", Cell. Phys. Biochem., vol. 14, 2004, pp. 311-324.
Lee et al., "Preclinical Efficacy and Mechanisms of Mesenchymal Stem Cells in Animal Models of Autoimmune Diseases", Immune Network, vol. 14, No. 2, Apr. 2014, pp. 81-88.
Levy et al., "Managment of Internal Fistulas in Crohn's Disease", Inflammatory Bowel Diseases, vol. 8, No. 2, Mar. 2002, pp. 106-111.
Li et al., "Human Umbilical Cord Mesenchymal Stem Cells Reduce Systemic Inflammation and Attenuate LPS-Induced Acute Lung Injury in Rats", Journal of Inflammation, vol. 9, No. 33, Sep. 2012, pp. 1-11.
Liu, et al. (2004) "Autologous Stem Cell Transplantation for Myocardial Repair," Am. J. Physiol. Heart Circ. Physiol. 287:H501-H511.
Lopez-Santalla et al. (2015). "Human Adipose-Derived Mesenchymal Stem Cells Modulate Experimental Autoimmune Arthritis by Modifying Early Adaptive T Cell Responses," Stem Cells, 33: 3493-3503.
Lund et al., "Effect of Growth Media and Serum Replacements on the Proliferation and Differentiation of Adipose-Derived Stem Cells", Cytotherapy, vol. 11, No. 2, 2009, pp. 189-197.
Matsubara, Hiroaki, "Risk to the Coronary Arteries of Intracoronary Stem Cell Infusion and G-CSF Cytokine Therapy", The Lancet, vol. 363, Mar. 6, 2004, pp. 746-747.
McIntosh et al., "The Immunogenicity of Human Adipose-Derived Cells: Temporal Changes in Vitro", Stem Cells, vol. 24, 2006, pp. 1246-1253.

(56) References Cited

OTHER PUBLICATIONS

Mei et al. (2007). "Prevention of LPS-Induced Acute Lung Injury in Mice by Mesenchymal Stem cells Overexpressing Angiopoietin 1," PLoS Medicine, vol. 4, Issue 9, pp. 1525-1537.
Mei et al., "Mesenchymal Stem Cells Reduce Inflammation while Enhancing Bacterial Clearance and Improving Survival in Sepsis", American Journal of Respiratory and Critical Care Medicine, vol. 182, Oct. 2010, pp. 1047-1057.
Minteer et al., "Adipose-Derived Mesenchymal Stem Cells: Biology and Potential Applications", Adv. Biochem. Eng. Biotechnol., vol. 129, 2013, pp. 59-71.
Mizuno et al., "Myogenic Differentiation by Human Processed Lipoaspirate Cells", Plastic and Reconstructive Sugery, vol. 109, No. 1, Jan. 2002, pp. 199-209.
Molendijk et al. (2014). "Disappointing durable remission rates in complex Crohn's disease fistula," Inflamm Bowel Dis. 20(11):2022-8.
Molendijk et al. (2015). "Allogeneic Bone Marrow-Derived Mesenchymal Stromal Cells Promote Healing of Refractory Perianal Fistulas in Patients With Crohn's Disease," Gastroenterology, vol. 149, pp. 918-927.
Morrisson et al., "The Biology of Hematopoietic Stem Cells", Annu. Rev. Cell Dev. Biol., vol. 11, 1995, pp. 35-71.
Nemeth et al., "Bone Marrow Stromal Cells Attenuate Sepsis via Prostaglandin E2-Dependent Reprogramming of Host Macrophages to increase their Interleukin-10 Production", Nature Medicine, vol. 15, No. 1, Jan. 2009, pp. 42-49.
Nielsen et al. (2009). "Diagnosis and management of fistulizing Crohn's disease," Nat Clin Pract Gastroenterol Hepatol. 6(2):92-106.
Non Final Office Action received for U.S. Appl. No. 14/017,152, dated May 14, 2015, 7 pages.
Non-Final Office Action received for U.S. Appl. No. 11/167,061, dated Feb. 3, 2011, 9 pages.
Non-Final Office Action received for U.S. Appl. No. 11/993,859, dated Apr. 22, 2013, 23 pages.
Non-Final Office Action received for U.S. Appl. No. 14/017,152, dated Aug. 12, 2014, 9 pages.
Non-Final Office Action received for U.S. Appl. No. 14/017,152, dated Jun. 23, 2016, 14 pages.
Non-Final Office Action received for U.S. Appl. No. 14/538,681, dated Aug. 17, 2016, 30 pages.
Notice of Allowance received for U.S. Appl. No. 11/993,859, dated Aug. 12, 2014, 9 pages.
Notice of Allowance received for U.S. Appl. No. 11/993,859, dated May 21, 2014, 9 pages.
Osawa et al., "Long-Term Lymphohematopoietic Reconstitution by a Single CD34-Low/Negative Hematopoietic Stem Cell", Science, vol. 273, Jul. 12, 1996, pp. 242-245.
Panes et al. (2016). "A phase III randomised controlled trial of Cx601, expanded allogeneic adipose-derived mesenchymal stem cells (eASC), for complex perianal fistulas in Crohn's disease," Journal of Crohn's and Colitis, Oral presentations, pp. S1.
Panés et al. (2016). "Expanded allogeneic adipose-derived mesenchymal stem cells (Cx601) for complex perianal fistulas in Crohn's disease: a phase 3 randomised, double-blind controlled trial," Lancet. 388(10051):1281-90.
Panes et al. (2017). "CX601, Allogeneic Expanded Adipose-derived Mesenchymal Stem Cells (EASC), for Complex Perianal Fistulas in Crohn's Disease: Long-term Results from a Phase III Randomized Controlled Trial," AGA Abstracts, pp. S-187.
Park et al. (2012). "Adipose-Derived Stem Cell Treatment for Persistent Perineal Wound in Complex Crohn's Perianal Abscess/Fistula," Gastroenterology, vol. 142, Issue 5, Supplement 1, pp. S-76, AGA Abstract 329.
Park et al. (2014). "Allogeneic Adipose-Derived Stem Cells for the Treatment of Crohn's Perianal Fistula: a Phase I/IIa Clinical Study," Gastroenterology, vol. 146, Issue 5, S-1016, SSAT Abstract 507.

Park et al. (2015). "Allogeneic adipose-derived stem cells for the treatment of perianal fistula in Crohn's disease: a pilot clinical trial," Colorectal Dis. 18(5):468-76.
Pascual et al., "Adipose-Derived Mesenchymal Stem Cells in Biosutures do not Improve Healing of Experimental Colonic Anastomoses", Brit. J. Surg., vol. 95, No. 9, 2008, pp. 1180-1184.
Pearson et al. (1995). "Azathioprine and 6-mercaptopurine in Crohn disease. A meta-analysis," Ann Intern Med. 15;123(2):132-42.
Penninckx et al., "Advancement Flap Plasty for the Closure of Anal and Recto-Vaginal Fistulas in Crohn's Disease", Acta Gastro-Enterolgica Belgica, vol. 64, Apr.-Jun. 2001, pp. 223-226.
Phillips, R. L., "Investigating the Genetic Control of Stem Cell Behavior", Curr. Top. Microbiol. Immunol., vol. 251, 2000, pp. 13-19.
Pitienger et al., "Multilineage Potential of Adult Human Mesenchymal Stem Cells", Science, vol. 284, Apr. 2, 1999, pp. 143-147.
Present et al. (1980). "Treatment of Crohn's disease with 6-mercaptopurine. A long-term, randomized, double-blind study," N Engl J Med, 302:981-987.
Present et al. (1999). "Infliximab for the treatment of fistulas in patients with Crohn's disease," N Engl J Med. 340(18):1398-405.
Puissant et al., "Immunomodulatory effect of human adipose tissue-derived adult stem cells: comparison with bone marrow mesenchymal stem cells," British Journal of Haematology, 2005, pp. 118-129, vol. 129.
Rajshekhar et al., "IFATS Collection: Adipose Stromal Cell Differentiation is Reduced by Endothelial Cell Contact and Paracrine Communication: Role of Canonical Wnt Signaling", Stem Cells., vol. 26, No. 10, 2008, pp. 2674-2681.
Ramalho-Santos et al., "Stemness: Transcriptional Profiling of Embryonic and Adult Stem Cells", Science, vol. 298, Oct. 18, 2002, pp. 597-600.
Requirement for Restriction/Election received for U.S. Appl. No. 11/993,859, dated Jul. 5, 2012, 11 pages.
Rius et al., "Gacilis Transposition in Complicated Perianal Fistula and Unhealed Perineal Wounds in Crohn's Disease", Eur. J. Surg., vol. 166, 2000, pp. 218-222.
Roach et al., "Methods for the Isolation and Maintenance of Murine Embryonic Stem Cells," Methods in Molecular Biology, 2002, pp. 1-16, vol. 185.
Rodriguez et al., "Autologous Stromal Vascular Fraction Therapy for Rheumatoid Arthritis: Rationale and Clinical Safety", International Archives of Medicine, Biomed Central Ltd, vol. 5, No. 5, Feb. 8, 2012, pp. 1-9.
Rogers et al., "Differentiation Factors Induce Expression of Muscle, Fat, Cartilage, and Bone in a Clone of Mouse Pluripotent Mesenchymal Stem Cells", The American Surgeon, vol. 61, No. 3, Mar. 1995, pp. 231-236.
Rojewski et al., "Phenotypic Characterization of Mesenchymal Stem Cells from Various Tissues", Trans. Med. Hemother., vol. 35, 2008, pp. 168-184.
Sanchez-Ramos et al., "Adult Bone Marrow Stromal Cells Differentiate into Neural Cells in Vitro", Experimental Neurology, vol. 164, 2000, pp. 247-256.
Sands eta I. (2004). "Infliximab maintenance therapy for fistulizing Crohn's disease," N Engl J Med. 350(9):876-85.
Sanz-Baro et al. (2015). "First-in-Human Case Study: Pregnancy in Women With Crohn's Perianal Fistula Treated With Adipose-Derived Stem Cells: A Safety Study," Stem Cells Transl Med., 4(6):598-602.
Schaffler et al., "Concise Review: Adipose Tissue-derived Stromal Cells—Basic and Clinical Implications for Novel Cell-based Therapies", Stem Cells, vol. 25, No. 4, Apr. 1, 2007, pp. 818-827.
Scharl et al. (2014). "Pathophysiology of fistula formation in Crohn's disease," World J Gastrointest Pathophysiol. 5(3):205-12.
Schreml et al., "Harvesting Human Adipose Tissue-Derived Adult Stem Cells: Resection Versus Liposuction", Cytotherapy, vol. 11, No. 7, 2009, pp. 947-957.
Schwartz et al. (2002). "The natural history of fistulizing Crohn's disease in Olmsted County, Minnesota," Gastroenterology. 122(4):875-80.
Schwartz et al. (2004). "Review article: The medical treatment of Crohn's perianal fistulas," Aliment Pharmacol Ther, 19:953-67.

(56) References Cited

OTHER PUBLICATIONS

Singer et al. (2011). "Mesenchymal stem cells: mechanisms of inflammation," Annu Rev Pathol. 6:457-78.
Solomon et al. (1993). "Combination ciprofloxacin and metronidazole in severe perianal Crohn's disease," Can J Gastroenterol, 7:571-3.
Stanford et al., "Rapidly Forming Apatitic Mineral in an Osteoblastic Cell Line (UMR 106-01 BSP)", The Journal of Biological Chemistry, vol. 270, No. 16, Apr. 21, 1995, pp. 9420-9428.
Thankamony et al., "Enforced Hematopoietic Cell E- and L-Selectin Ligand (HCELL) Expression Primes Transendothelial Migration of Human Mesenchymal Stem Cells", PNAS, vol. 108, 2011, pp. 2258-2263.
Thia et al. (2009). "Ciprofloxacin or metronidazole for the treatment of perianal fistulas in patients with Crohn's disease: a randomized, double-blind, placebo-controlled pilot study," Inflamm Bowel Dis, 15:17-24.
Third Party Submissions dated May 15, 2014, submitted in U.S. Appl. No. 14/017,152, 13 pages.
Tholpady et al., "Adipose Tissue: Stem Cells and Beyond", Clin. Plast. Surg., vol. 33, No. 1, 2006, pp. 55-62.
Tigenix (2016). "Cx601 Crohn's disease and perianal fistulas," Retrieved from http://tigenix.com/en/page/14/cx601, 5 pages.
Torensma et al., "The Impact of Cell Source, Culture Methodology, Culture Location and Individual Donors on Gene Expression Profiles of Bone Marrow-Derived and Adipose-Derived Stromal Cells", Stem Cell Dev., vol. 22, No. 7, 2013, pp. 1086-1096.
Van Assche et al. (2010). "The second European evidence-based Consensus on the diagnosis and management of Crohn's disease: Special situations," J Crohns Colitis. 4(1):63-101.
Van et al., "Cytological and Enzymological Characterization of Adult Human Adipocyte Precursors in Culture", J. Clin. Invest., vol. 58, No. 3, 1976, pp. 699-704.
Wabitsch et al., "IGF-1- and IGFBP-3-Expression in Cultured Human Preadipocytes and Adipocytes", Horm. Metab. Res., vol. 32, 2000, pp. 555-559.
Wagner et al., "Comparative Characteristics of Mesenchymal Stem Cells from Human Bone Marrow, Adipose Tissue, and Umbilical Cord Blood", Experimental Hematology, vol. 33, 2005, pp. 1402-1416.
Wakitani et al., "Myogenic Cells Derived from Rat Bone Marrow Mesenchymal Stem Cells Exposed to 5-Azacytidine", Muscle & Nerve, vol. 18, Dec. 1995, pp. 1417-1426.
Wan Safwani et al., "The Changes of Stemness Biomarkers Expression in Human Adipose-Derived Stem Cells During Long-Term Manipulation", Biotechnology and Applied Biochemistry, vol. 58, No. 4, Jul./Aug. 2011, pp. 261-270.
Winter et al., "Cartilage-Like Gene Expression in Differentiated Human Stem Cell Spheroids. A Comparison of Bone Marrow-Derived and Adipose Tissue-Derived Stromal Cells", Arthritis and Rheumatism vol. 48, No. 2, 2003, pp. 418-429.
Xu et al., "Connective Tissue Growth Factor in Regulation of RhoA Mediated Cytoskeletal Tension Associated Osteogenesis of Mouse Adipose-Derived Stromal Cells", PLoS One., vol. 5, No. 6, 2010, e11279 page.
Xu, Jianguo, et al., "Prevention of endotoxin-induced systemic response by bone marrow-derived mesenchymal stem cells in mice," American Journal of Physiology, Lung Cellular and Molecular Physiology, 2007, pp. L131-L 141, vol. 293.
Yañez, Rosa, et al.; "Adipose Tissue-Derived Mesenchymal Stem Cells Have In Vivo Immunosuppressive Properties Applicable for the Control of the Graft-Versus-Host Disease," Stem Cells, 2006, pp. 2582-2591, vol. 24.
Yoo et al., "The Role of Osteochondral Progenitor Cells in Fracture Repair", Clinical Orthopaedics and Related Research, vol. 355S, Oct. 1998, pp. S73-S81.
Yoshimura et al., "Characterization of Freshly Isolated and Cultured Cells Derived From the Fatty and Fluid Portions of Liposuction Aspirates", Journal of Cellular Physiology, vol. 208, 2006, pp. 64-76.

Young et al., "Use of Mesenchymal Stem Cells in a Collagen Matrix for Achilles Tendon Repair", J. Ortho. Res., vol. 16, No. 4, 1998, pp. 406-413.
Zannetiino et al., "Multipotential Human Adipose-Derived Stromal Stem Cells Exhibit a Perivascular Phenotype In Vitro and In Vivo", J. Cell. Phys., vol. 214, 2008, pp. 413-421.
Zhao et al., "The Effect of Serial Passaging on the Proliferation and Differentiation of Bovine Adipose-Derived Stem Cells", Cells Tissues Organs, vol. 195, 2011, pp. 414-427.
Zilberfarb et al., "Human Immortalized Brown Adipocytes Express Functional Beta3-Adrenoceptor Coupled to Lipolysis", J. Cell. Sci., vol. 110, 1997, pp. 801-807.
Zimmerlin et al., "Stromal Vascular Progenitors in Adult Human Adipose Tissue", Cytometry, vol. 77A, No. 1, 2010, pp. 22-30.
Zuk et al., "Human Adipose Tissue is a Source of Multipotent Stem Cells", Molecular Biology of the Cell, vol. 13, 2002, pp. 4279-4295.
Abedi et al. (2005). "Critical variables in the conversion of marrow cells to skeletal muscle," Blood, 106: 1488-1494.
Fouillard et al. (2003). "Engraftment of allogeneic mesenchymal stem cells in the bone marrow of a patient with severe idiopathic aplastic anemia improves stroma," Leukemia, 17: 474-476.
Huang et al. (2010). "Differentiation of Allogeneic Mesenchymal Stem Cells Induces Immunogenicity and Limits Their Long-Term Benefits for Myocardial Repair," Circulation, 122: 2419-2429.
Lendeckel et al., "Autologous Stem Cells (Adipose) and Fibrin Glue Used to Treat Widespread Traumatic Calvarial Defects: Case Report", Journal of Cranio Maxillofacial Surgery, vol. 32, No. 6, Dec. 2004, pp. 370-373.
Silva et al. (2005). "Mesenchymal Stem Cells Differentiate into an Endothelial Phenotype, Enhance Vascular Density, and Improve Heart Function in a Canine Chronic Ischemia Model," Circulation, 111:150-156.
Toma et al. (2002). "Human Mesenchymal Stem Cells Differentiate to a Cardiomyocyte Phenotype in the Adult Murine Heart," Circulation, 105:93-98.
Cx611-0101, eASCs intravenous administration to refractory rheumatoid arthritis patients. ClinicalTrials.gov, U.S. National Library of Medicine, Aug. 13, 2012 [retrieved on Apr. 22, 2018]. Retrieved from the Internet: <URL:https://clinicaltrials.gov/ct2/show/NCT01663116>, 10 pages.
De Ugarte et al., (2003). "Differential expression of stem cell mobilization-associated molecules on multi-lineage cells from adipose tissue and bone marrow," Immunology Letters 89:267-270.
Gimble et al., (2003). "Adipose-derived adult stem cells: isolation, characterization, and differentiation potential," Cytotherapy, 5(5):362-369.
Gronthos et al., (2001). "Surface Protein Characterization of Human Adipose Tissue-Derived Stormal Cells," Journal of Cellular Physiology, vol. 189: 55-63.
Le Blanc et al., (2004). "Treatment of sever acute graft-versus-host disease with third party haploidentical mesenchymal stem cells," The Lancet, vol. 363, pp. 1439-1441.
Walmsley, G.G., et al., (2015). "High-Throughput Screening of Surface Marker Expression on Undifferentiated and Differentiated Human Adipose-Derived Stromal Cells," Tissue Eng Part A, 21(15-16): p. 2281-2291.
Aggarwal et al. (2005), "Human mesenchymal stem cells modulate allogeneic immune cell responses," Blood, vol. 105, No. 4, pp. 1815-1822.
Alessandroni et al. (2011). "Local injection of infliximab in severe fistulating perianal Crohn's disease: an open uncontrolled study," Tech Coloproctol, 15:407-412.
Be the Match, Haploidentical Transplant, retrieved from the internet, Feb. 14, 2019: https://bethematch.org/patients-and-families/about-transplant/what-is-a-bone-marrow-transplant/haploidentical-transplant/.
Bouffi et al., (2009). "Multipotent mesenchymal stromal cells and rheumatoid arthritis: risk or benefit?", Rheumatology, 2009, vol. 48, No. 10, pp. 1185-1189.
Deng et al. (2004), "Allogeneic bone marrow-derived flk-1 Sca-1 mesenchymal stem cells leads to stable mixed chimerism and donor-specific tolerance," Experimental Hematology, vol. 32, pp. 861-867.
EMA press release (2017). "New medicine to treat periana fistulas in patients with Crohn's disease," 2 pages.

(56) References Cited

OTHER PUBLICATIONS

Fibrin Glue Injection for Treatment of Perianal Fistula, (2002). Kaiser Permanente Clinical Review Criteria, retrieved from the internet: https://provider.ghc.org/all-sites/clinical/criteria/pdf/fibrin_glue.pdf.

Garcia Olmo (2007). "Expanded adipose-derived stem cells (Cx401) for the treatment of complex perianal fistula, a phase II clinical trial," Gastroenterology, 2 pages.

Kurozumi et al., (2004). "BDNF Gene-Modified Mesenchymal Stem Cell Promote Functional Recovery and Reduce Infarct Size in the Rat Middle Cerebral Artery Occlusion Model," Molecular Therapy, 9(2):189-197.

Le Blanc et al. (2003). "HLA expression and immunologic properties of differentiated and undifferentiated mesenchymal stem cells," Exp Hematol, 31(10):890-896.

Maneesh (2014). "Nonmyeloablative Stem Cell Therapy for Perianal Fistulizing Crohn's Disease: A Systematic Review of Safety and Efficacy," Gastroenterology, 2 pages.

Pittenger et al. (1999). "Multilineage potential of adult human mesenchymal stem cells," Science, 284(5411):143-147.

Rizk et al. (2016). "Heterogeneity in Studies of Mesenchymal Stromal Cells to Treat or Prevent Graft-versus-Host Disease: A Scoping Review of the Evidence," Biol Blood Marrow Trans, 22(8):1416-1423.

Search Report received for EP18152520, dated May 17, 2018, 11 pages.

Tigenix (2015). "Tigenix Living Medicines, Corporate Presentation, Feb. 2015," 40 pages.

Tigenix (2015). "Tigenix Living Medicines, Corporate Presentation, Mar. 2015," 39 pages.

Tigenix (2015). "Tigenix Living Medicines, Corporate Presentation, Oct. 2015," 40 pages.

Tigenix (2015). "Tigenix Living Medicines, Corporate Presentation, Sep. 2015," 41 pages.

Tigenix (2016). "Tigenix Living Medicines, Corporate Presentation, Jan. 2016," 39 pages.

\* cited by examiner

ADIPOSE TISSUE-DERIVED STROMAL STEM CELLS FOR USE IN TREATING REFRACTORY COMPLEX PERIANAL FISTULAS IN CROHN'S DISEASE

CROSS-REFERENCE TO RELATED APPLICATIONS

This application claims the benefit of United Kingdom Patent Application No. 1604304.4, filed Mar. 14, 2016, which is hereby incorporated by reference in its entirety.

FIELD OF THE INVENTION

This invention relates to adipose tissue-derived stem cells for use in treating refractory complex perianal fistulas in patients with Crohn's Disease.

BACKGROUND TO THE INVENTION

Generally, a fistula is an abnormal connection or passageway between organs or vessels that normally do not connect. Fistulae can develop in various parts of the body. For example, types of fistulae, named for the areas of the body in which they occur, include anorectal fistula or fistula-in-ano or fecal fistula (between the rectum or other anorectal area and the skin surface), arteriovenous fistula or A-V fistula (between an artery and vein), biliary fistula (between the bile ducts to the skin surface, often caused by gallbladder surgery), cervical fistula (abnormal opening in the cervix), craniosinus fistula (between the intracranial space and a paranasal sinus), enteroenteral fistula (between two parts of the intestine), enterocutaneous fistula (between the intestine and the skin surface, namely from the duodenum or the jejunum or the ileum), enterovaginal fistula (between the intestine and the vagina), gastric fistula (between the stomach to the skin surface), metroperitoneal fistula (between the uterus and peritoneal cavity), perilymph fistula (a tear between the membranes between the middle and inner ears), pulmonary arteriovenous fistula (between an artery and vein of the lungs, resulting in shunting of blood), rectovaginal fistula (between the rectum and the vagina), umbilical fistula (between the umbilicus and gut), tracheoesophageal fistula (between the breathing and the feeding tubes) and vesicovaginal fistula (between the bladder and the vagina). Causes of fistulae include trauma, complications from medical treatment and disease.

Treatment for fistulae varies depending on the cause and extent of the fistula, but generally involves surgical intervention. Various surgical procedures are commonly used, most commonly fistulotomy, placement of a seton (a cord that is passed through the path of the fistula to keep it open for draining), or an endorectal flap procedure (where healthy tissue is pulled over the internal side of the fistula to keep feces or other material from reinfecting the channel). Surgery for anorectal fistulae is not without side effects, including recurrence, reinfection, and incontinence.

Inflammatory bowel diseases, such as Crohn's disease and ulcerative colitis, are the leading causes of anorectal, enteroenteral, and enterocutaneous fistulae. The reported incidence of fistula in Crohn's disease ranges from 17% to 50%. Management of fistulae in patients with Crohn's disease continues to present an extremely challenging problem since many such fistulae do not respond to available treatments. Such fistulae and their recurrence are a very distressing complication that significantly reduces the quality of life of affected patients. Recent improvements in medical treatment (e.g., treatment with Infliximab®) and expert surgical management have decreased the need for complicated surgery. However, many patients are not cured. Failure of fistulae to heal is probably due to the suboptimal quality of tissues that have been affected by Crohn's disease. Indeed, Crohn's fistulae provide a model system for wound healing under some of the worst possible conditions.

Perianal fistulas are a common complication of Crohn's disease,[41] which are estimated to affect up to 28% of patients in the first two decades after diagnosis,[42,43] particularly those with colonic disease and rectal involvement.[44] They severely impair patients' quality of life and cause considerable morbidity.[45,46] Approximately 70-80% of perianal fistulas are complex,[43,47] and these are challenging to treat since they are particularly refractory to conventional treatment strategies (antibiotics, immunosuppressants) and anti-tumor necrosis factor (anti-TNF) therapies.[48-412] Furthermore, 60-70% of patients relapse on stopping treatment,[413-417] and only a minority of patients achieve long-term remission.[418]

Failure of or intolerability to medical therapy can ultimately result in debilitating surgical approaches, such as diverting stoma or proctectomy.[419] Therefore, there remains a huge unmet need for alternative medical treatments.

Mesenchymal stromal cells (MSCs) are non-hematopoietic stromal cells that are able to differentiate into mesenchymal tissues such as bone, cartilage, muscle, ligament, tendon, and adipose. MSCs can be easily isolated from tissues such as bone marrow or adipose tissue and rapidly expanded in culture. WO-A-2006/136244 describes the treatment of fistulae using adipose tissue-derived stromal stem cell-containing compositions. Adipose-derived mesenchymal stromal cells are a promising new therapeutic approach, which may be useful for the treatment of complex perianal fistulas due to their anti-inflammatory and tissue-regenerating potential.[420-422] Initial proof of concept was previously obtained in an open-label phase ½a clinical study of allogeneic, expanded adipose-derived stem cells (eASC, Cx601) in 24 Crohn's disease patients with complex perianal fistulas with 56.3% of patients showing complete closure of the external opening and the absence of collections measured by MRI of the treated fistula 24 weeks after treatment.[423]

Complex perianal fistulas in Crohn's disease are particularly challenging to treat and there remains a need for establishing clinically proven therapies for the treatment of complex perianal fistulas in Crohn's Disease.

SUMMARY OF THE INVENTION

The invention relates to the provision of clinically-proven therapies for treating refractory complex perianal fistulae in Crohn's Disease, based on the results of a multicenter, double-blind, placebo-controlled study evaluated the efficacy and safety of eASC in 212 adults with Crohn's disease and treatment-refractory, draining complex perianal fistulas. The Examples herein describe the first placebo-controlled phase 3 study evaluating the efficacy and safety of expanded allogeneic adipose-derived stem cells alone or added on to current medical therapy for treatment-refractory complex perianal fistulas in Crohn's disease patients. The results reported herein are the 24-week primary and secondary endpoints.

The new clinical trial data surprisingly revealed that adipose-derived stem cells treat multiple tract complex perianal fistulae especially effectively. The data also show that the numerically greatest effect of the cells was observed in patients who were receiving neither or both anti-TNF and immunosuppressant therapies at the time of fistula preparation. Additionally, clinical remission was achieved surprisingly soon after treatment, with the median time to clinical remisison in the treatment group being 6.7 weeks. Similarly, the median time to response was 6.3 weeks. Improvement in perianal disease activity index (PDAI) was significantly greater at weeks 6, 12 and 18. Overall, the data reveal that allogeneic eASCs are a surprisingly effective therapy for complex perianal fistulae in Crohn's Disease patients, whereby a single adminstration is able to provide a rapid and sustained therapeutic effect even in the most difficult to treat, very complex fistulae, where previous drug therapy has failed.

A first aspect of the invention provides expanded allogeneic adipose tissue-derived stromal stem cells for use in a method of treating a refractory complex perianal fistula in a patient having Crohn's disease.

A second aspect of the invention provides for use of expanded allogeneic adipose tissue-derived stromal stem cells in the manufacture of a medicament for treating a refractory complex perianal fistula in a patient having Crohn's disease.

A third aspect of the invention provides a method of treating a refractory complex perianal fistula in a patient having Crohn's disease, in a patient in need of such treatment, comprising the step of administering expanded allogeneic adipose tissue-derived stromal stem cells to the fistula.

Also disclosed herein, among other things, are adipose tissue-derived stromal stem cell-containing compositions. The adipose tissue-derived stromal stem cell-containing compositions described herein have a distinct phenotype and exhibit a beneficial homogeneity of phenotype, thus making them more suitable for use in treating fistulae. The adipose tissue-derived stromal stem cell-containing compositions may be formulated with solutions or other substances to serve as pharmaceuticals or medical devices, e.g., as sutures or adhesives. Further, provided are novel methods of treating complex perianal fistulae using adipose tissue-derived stromal stem cells, as well as kits for the practice of the same.

DETAILED DESCRIPTION OF THE INVENTION

1. Definitions

Figure 1:
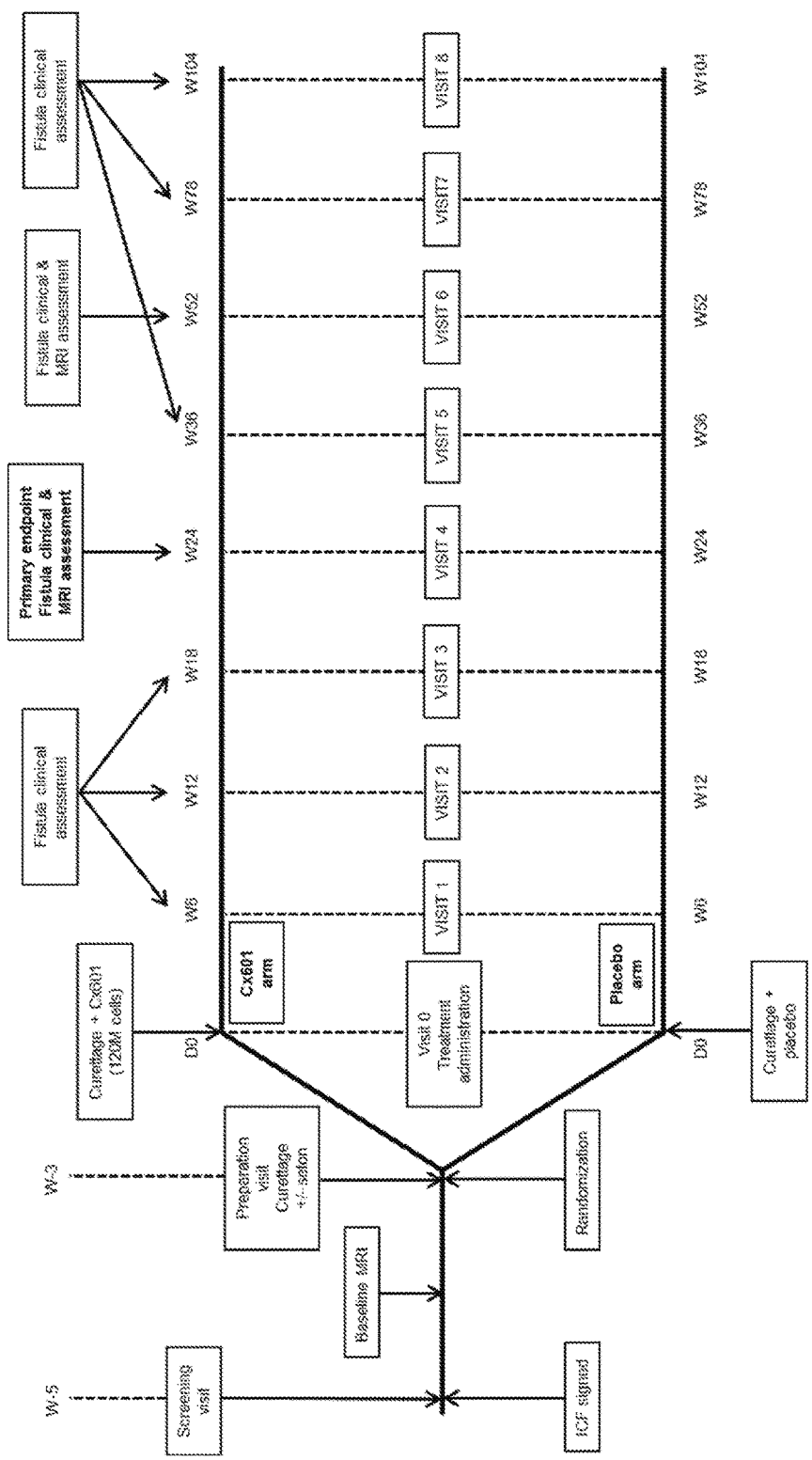
FIG. 1: depicts the Phase III clinical study design. Cx601, allogeneic, expanded, adipose-derived stem cells; ICF, informed consent form; MRI, magnetic resonance imaging.

As used herein, the following terms and phrases shall have the meanings set forth below. Unless defined otherwise, all technical and scientific terms used herein have the same meaning as commonly understood to one of ordinary skill in the art to which this invention belongs.

The articles "a" and "an" refer to one or to more than one (i.e., to at least one) of the grammatical object of the article. By way of example, "an element" means one element or more than one element.

By "adipose tissue" is meant any fat tissue. The adipose tissue may be brown or white adipose tissue, derived from subcutaneous, omental/visceral, mammary, gonadal, or other adipose tissue site. Typically, the adipose tissue is subcutaneous white adipose tissue. Such cells may comprise a primary cell culture or an immortalized cell line. The adipose tissue may be from any organism having fat tissue. Typically, the adipose tissue is mammalian, most typically the adipose tissue is human. A convenient source of adipose tissue is from liposuction surgery, however, the source of adipose tissue or the method of isolation of adipose tissue is not critical to the invention.

"Adipose tissue-derived stromal stem cells" or "ASCs" refers to mesenchymal stem cells that originate from the stromal fraction of adipose tissue, generally from human adipose tissue (hASCs).

The term "adhesive" refers to any substance that unites or bonds surfaces together; e.g., a glue.

The term "biological medicinal product" shall be taken to mean a protein or nucleic acid-based pharmaceutical substance for therapeutic use, which is typically produced by means other than direct extraction from a native (nonengineered) biological source.

The term "cellular composition" refers to a preparation of cells, which preparation may include, in addition to the cells, non-cellular components such as cell culture media, e.g. proteins, amino acids, nucleic acids, nucleotides, co-enzyme, anti-oxidants, metals and the like. Furthermore, the cellular composition can have components which do not affect the growth or viability of the cellular component, but which are used to provide the cells in a particular format, e.g., as polymeric matrix for encapsulation or a pharmaceutical preparation.

A "complex perianal fistula" is a perianal fistula having one or more of:
  (i) high inter-, trans-, extra- or supra-sphincteric origin;
  (ii) ≥2 external openings; or
  (iii) associated collections.

The complex perianal fistula may optionally have a maximum of 2 internal and 3 external openings. Further, the complex perianal fistula may have been draining for at least 6 weeks prior to treatment according to the invention.

The term "culture" refers to any growth of cells, organisms, multicellular entities, or tissue in a medium. The term "culturing" refers to any method of achieving such growth, and may comprise multiple steps. The term "further culturing" refers to culturing a cell, organism, multicellular entity, or tissue to a certain stage of growth, then using another culturing method to bring said cell, organism, multicellular entity, or tissue to another stage of growth. A "cell culture" refers to a growth of cells in vitro. In such a culture, the cells proliferate, but they do not organize into tissue per se. A "tissue culture" refers to the maintenance or growth of tissue, e.g., explants of organ primordial or of an adult organ in vitro so as to preserve its architecture and function. A "monolayer culture" refers to a culture in which cells multiply in a suitable medium while mainly attached to each other and to a substrate. Furthermore, a "suspension culture" refers to a culture in which cells multiply while suspended in a suitable medium. Likewise, a "continuous flow culture" refers to the cultivation of cells or explants in a continuous flow of fresh medium to maintain cell growth, e.g. viability. The term "conditioned media" refers to the supernatant, e.g. free of the cultured cells/tissue, resulting after a period of time in contact with the cultured cells such that the media has been altered to include certain paracrine and/or autocrine factors produced by the cells and secreted into the culture. A "confluent culture" is a cell culture in which all the cells are in contact and thus the entire surface of the culture vessel is covered, and implies that the cells have also reached their maximum density, though confluence does not necessarily mean that division will cease or that the population will not increase in size.

The term "culture medium" or "medium" is recognized in the art, and refers generally to any substance or preparation used for the cultivation of living cells. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. Similarly, a powder mixture that when mixed with water or other liquid becomes suitable for cell culture, may be termed a "powdered medium". "Defined medium" refers to media that are made of chemically defined (usually purified) components. "Defined media" do not contain poorly characterized biological extracts such as yeast extract and beef broth. "Rich medium" includes media that are designed to support growth of most or all viable forms of a particular species. Rich media often include complex biological extracts. A "medium suitable for growth of a high density culture" is any medium that allows a cell culture to reach an OD600 of 3 or greater when other conditions (such as temperature and oxygen transfer rate) permit such growth. The term "basal medium" refers to a medium which promotes the growth of many types of microorganisms which do not require any special nutrient supplements. Most basal media generally comprise of four basic chemical groups: amino acids, carbohydrates, inorganic salts, and vitamins A basal medium generally serves as the basis for a more complex medium, to which supplements such as serum, buffers, growth factors, lipids, and the like are added. Examples of basal media include, but are not limited to, Eagles Basal Medium, Minimum Essential Medium, Dulbecco's Modified Eagle's Medium, Medium 199, Nutrient Mixtures Ham's F-10 and Ham's F-12, Mc Coy's 5A, Dulbecco's MEM/F-I 2, RPMI 1640, and Iscove's Modified Dulbecco's Medium (IMDM).

The terms "comprise" and "comprising" are used in the inclusive, open sense, meaning that additional elements may be included.

The term "Cx601" refers to a cell suspension in aseptic buffered saline solution containing human expanded adipose-derived stem cells (eASCs) of allogeneic origin. These cells are provided in disposable vials with no preservative agents. The cells are given at a dose of 120 million cells (5 million cells/mL) for intralesional injection.

The term "differentiation" refers to the formation of cells expressing markers known to be associated with cells that are more specialized and closer to becoming terminally differentiated cells incapable of further division or differentiation. For example, in a pancreatic context, differentiation can be seen in the production of islet-like cell clusters containing an increased proportion of beta-epithelial cells that produce increased amounts of insulin. The terms "further" or "greater" differentiation refers to cells that are more specialized and closer to becoming terminally differentiated cells incapable of further division or differentiation than the cells from which they were cultured. The term "final differentiation" refers to cells that have become terminally differentiated cells incapable of further division or differentiation.

The term "expanded" as used herein when referring to cells shall be taken to have its usual meaning in the art, namely cells that have been proliferated in vitro. Methods for the preparation of eASCs are known in the art, for example as described in WO2007/039150. An ASC can be expanded to provide a population of cells that retain at least one biological function of the ASC, typically the ability to adhere to a plastic surface, under standard culture conditions. The expanded population of cells may retain the ability to differentiate into one or more cell types.

The term "fistula" refers to any abnormal passage or communication or connection, usually between two internal organs or leading from an internal organ to the surface of the body. Examples of fistulae include, but are not limited to, anorectal fistula or fistula-in-ano or fecal fistula, arteriovenous fistula or A-V fistula, biliary fistula, cervical fistula, craniosinus fistula, enteroenteral fistula, enterocutaneous fistula, enterovaginal fistula, gastric fistula, metroperitoneal fistula perilymph, pulmonary arteriovenous fistula, rectovaginal fistula, umbilical fistula, tracheoesophageal fistula and vesicovaginal fistula. The invention relates to perianal fistula.

The term "including" is used herein to mean "including but not limited to". "Including" and "including but not limited to" are used interchangeably.

"Marker" refers to a biological molecule whose presence, concentration, activity, or phosphorylation state may be detected and used to identify the phenotype of a cell.

"Mesenchymal stromal cells" (also referred to herein as "MSCs") are multipotent stromal cells (i.e. they are cells which are capable of giving rise to multiple different types of cells), typically derived from connective tissue, and are non-hematopoietic cells. MSCs have the capacity to differentiate into or towards somatic cells such as mesodermal cells (e.g. adipose, chondrocytes, osteoblasts) and optionally into or towards endodermal and/or ectodermal cell types or lineages. Typically the cells have the capacity to differentiate into or towards at least two or all cell types selected from the group consisting of adipocytic, chondroblastic and osteoblastic lineages.

ASCs are a type of MSC that are obtained from the stromal fraction of the adipose tissue. MSCs and ASCs are adherent to plastic under standard culture conditions.

A "patch" is a dressing or covering applied to cover or protect a wound or other sore.

A "patient", "subject" or "host" to be treated by the subject method may mean either a human or a non-human animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. The term "phenotype" refers to the observable characteristics of a cell, such as size, morphology, protein expression, etc.

The term "progenitor cell" refers to a cell that has the capacity to create progeny that are more differentiated than itself. For example, the term may refer to an undifferentiated cell or cell differentiated to an extent short of final differentiation which is capable of proliferation and giving rise to more progenitor cells having the ability to generate a large number of mother cells that can in turn give rise to differentiated, or differentiable daughter cells. In a preferred embodiment, the term progenitor cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. By this definition, stem cells may also be progenitor cells, as well as the more immediate precursors to terminally differentiated cells.

"Proliferation" refers to an increase in cell number. "Proliferating" and "proliferation" refer to cells undergoing mitosis.

"Refractory" shall be taken to mean having no significant clinical benefit when used in the treatment of a diseases e.g. no significant improvement or amelioration of symptoms.

The term "remission" refers to the successful treatment of the fistula. "Clinical remission" is closure of all treated external openings that were draining at baseline, despite gentle finger compression. The time to clinical remission is defined as the time from treatment start to the first patient assessment with clinical remission. "Combined remission" is this clinical remission plus confirmation by MRI (magnetic resonance imaging) of the absence of collections greater than 2 cm in the treated perianal fistulas, in at least 2 of 3 dimensions. This is typically confirmed by blinded central MRI reading. The absence of collections or abscesses is important because if not cured, these will lead to a new fistula.

The term "response" refers to the closure of at least 50% of all treated external openings that were draining at baseline, despite gentle finger compression (i.e. as clinically assessed). Response is therefore met when 1 EO is closed if the number of EOs at basline is 1 or 2, and is met when 2 EOs are closed if 3 EOs were present at baseline. The time to response is defined as the time from treatment start to the first assessment of response.

The term "relapse" refers to, in patients with Clincial Remission at the previous assessment, re-opening of any of the treated external openings with active drainage as clinically assessed, or the development of a perianal collection greater than 2 cm of the treated perianal fistula(s) as confirmed by MRI.

As used herein, the term "solution" includes a pharmaceutically acceptable carrier or diluent in which the cells of the invention remain viable.

The term "substantially pure", with respect to adipose tissue-derived stem cell populations, refers to a population of adipose tissue-derived stem cell cells that is at least about 75%, typically at least about 85%, more typically at least about 90%, and most typically at least about 95% pure, with respect to adipose tissue-derived stromal stem cells making up a total cell population. Recast, the term "substantially pure" refers to a population of adipose tissue-derived stromal stem cells of the present invention that contain fewer than about 20%, more typically fewer than about 10%, most typically fewer than about 5%, of lineage committed cells in the original unamplified and isolated population prior to subsequent culturing and amplification.

"Support" as used herein refers to any device or material that may serve as a foundation or matrix for the growth of adipose tissue-derived stromal stem cells.

The term "suture" refers to a thread or fiber or other fastening material that can be used to sew a wound together.

A single "tract" fistula is has one internal opening and one external opening. A fistula with "multiple tracts" has more than 1 external opening and/or more than 1 internal opening. Therefore a multiple tract fistula has different branches. Each external opening typically represents a tract.

The term "treating" as used herein refers to repairing a fistula or wound, as well as preventing a fistula or wound from worsening or recurring.

"Therapeutic agent" or "therapeutic" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents are known in the art and may be identified by their effects. Certain therapeutic agents are capable of regulating cell proliferation and differentiation. Examples include chemotherapeutic nucleotides, drugs, hormones, non-specific (non-antibody) proteins, oligonucleotides (e.g., antisense oligonucleotides that bind to a target nucleic acid sequence (e.g., mRNA sequence)), peptides, and peptidomimetics.

2. Adipose Tissue-Derived Stromal Stem Cell-Containing Compositions

The invention involves adipose tissue-derived stromal stem cell-containing compositions with certain characteristics, such as a particular phenotype. For example, the adipose tissue-derived stromal stem cells in a cellular composition of the invention may be characterized by cell surface marker expression, size, glucose consumption, lactate production, and cell yield/viability. Yet another aspect of the present invention concerns adipose tissue-derived stromal stem cell-containing compositions which include, as a cellular component, substantially pure preparations of adipose tissue-derived stromal stem cells having a particular phenotype, or the progeny thereof. Adipose tissue-derived stromal stem cell-containing compositions of the present invention include not only substantially pure populations of the progenitor cells, but can also include cell culture components, e.g., culture media including amino acids, metals, coenzyme factors, as well as small populations of other stromal cells, e.g., some of which may arise by subsequent differentiation of cells of the invention. Furthermore, other non-cellular components can include those which render the cellular component suitable for support under particular circumstances, e.g., implantation, e.g., continuous culture, or suitable for use as a biomaterial or pharmaceutical composition.

In certain embodiments, the adipose tissue-derived stromal stem cell-containing compositions are produced through the culture methods described in Section 3.

The preferred ASCs are Cx601 cells. The proposed (but not confirmed) International Nonproprietary Name for these cells is "Adalextemcel".

The ASCs are adherent to plastic under standard culture conditions.

Expanded ASC (eASC) exhibit a fibroblast-like morphology in culture.

Specifically, these cells are big and are morphologically characterised by a shallow cell body with few cell projections that are long and thin. The nucleus is large and round with a prominent nucleolus, giving the nucleus a clear appearance. Most of eASCS display this spindle-shaped morphology, but it is usual that some of the cells acquire polygonal morphologies (Zuk et al., 2002).

The Cx601 eASCs are positive for the surface markers HLA I, CD29, CD44, CD59, CD73, CD90, and CD105. One embodiment therefore provides an eASC-containing composition wherein at least about 80%, at least about 90% or at least about 95%, or typically at least about 96%, 97%, 98% or 99% of the eASCs express the surface markers HLA I, CD29, CD44, CD59, CD73, CD90, and CD105. Typically, at least about 90% of the eASCs express the surface markers HLA I, CD29, CD44, CD59, CD73, CD90, and CD105. More typically, at least about 95% of the eASCs express the surface markers HLA I, CD29, CD44, CD59, CD73, CD90, and CD105.

The CX601 eASCs are negative for HLAII, CD11b, CD11c, CD14, CD45, CD31, CD34, CD80 and CD86. One embodiment therefore provides an eASC-containing composition wherein fewer than about 5% of the eASCs express the surface markers HLAII, CD11b, CD11c, CD14, CD45, CD31, CD34, CD80 and CD86. More typically, fewer than about 4%, 3% or 2% of the eASCs express the surface markers HLAII, CD11b, CD11c, CD14, CD45, CD31, CD34, CD80 and CD86. In one embodiment, fewer than about 1% of the eASCs express the surface markers HLAII, CD11b, CD11c, CD14, CD45, CD31, CD34, CD80 and CD86.

In some embodiments the eASCs may express one or more (e.g. two or more, three or more, four or more, five or more, six or seven) of HLA I, CD29, CD44, CD59, CD73, CD90, and CD105. In some embodiments, the eASCs may not express one or more (e.g. two or more, three or more, four or more, five or more, six or more, seven or eight) of HLAII, CD11b, CD11c, CD14, CD45, CD31, CD34, CD80. In some embodiments, the eASCs express four or more of HLA I, CD29, CD44, CD59, CD73, CD90, and CD105 and do not express four or more of HLAII, CD11b, CD11c, CD14, CD45, CD31, CD34, CD80.

Expanded human ASCs according to certain embodiments of the invention are described in DelaRosa et al ("Requirement of IFN-gamma-mediated indoleamine 2,3-dioxygenase expression in the modulation of lymphocyte proliferation by human adipose-derived stem cells."; Tissue Eng Part A. 2009 October; 15(10):2795-806. doi: 10.1089/ten.TEA.2008.0630) and in Lopez-Santalla et al 2015 ("Human Adipose-Derived Mesenchymal Stem Cells Modulate Experimental Autoimmune Arthritis by Modifying Early Adaptive T Cell Responses." STEM CELLS, 33: 3493-3503. doi: 10.1002/stem.2113).

In one embodiment (as described in Lopez-Santalla et al 2015), human adipose tissue aspirates from healthy donors were washed twice with phosphate-buffered saline and digested with 0.075% collagenase (Type I; Invitrogen). The digested sample was washed with 10% fetal bovine serum (FBS), treated with 160 mM NH4Cl to eliminate the remaining erythrocytes, and suspended in culture medium [Dulbecco's modified Eagle's medium (DMEM) with 10% FBS. Cells were seeded (2-3·104 cells/cm2) in tissue culture flasks and expanded (37° C., 5% CO2) with change of culture medium every 3-4 days. Cells were transferred to a new flask (103 cells/cm2) when they reached 90% confluence. Cells were expanded up to duplication 12-14 and frozen. Experiments were performed with cells from two male and two female adult donors at population doublings 12-14. ASCs were thawed from the same cryobanks and seeded before each experiment. ASCs were defined according to the criteria of the International Society for Cellular Therapy: being positive for HLA-I, CD73, CD90, and CD105 and negative for CD11b, CD14, CD31, CD34, and CD45.

In another embodiment (as described by DelaRosa et al 2009), lipoaspirates obtained from human adipose tissue from healthy adult donors were washed twice with PBS, and digested at 378 C for 30 min with 18U=mL of collagenase type I in PBS. One unit of collagenase liberates 1 mM of L-leucine equivalents from collagen in 5 h at 378 C, pH 7.5 (Invitrogen, arlsbad, CA). The digested sample was washed with 10% of fetal bovine serum (FBS), treated with 160 mM ClNH4, suspended in culture medium (DMEM containing 10% FBS), and filtered through a 40-mm nylon mesh. Cells were seeded (2-3_104 cells=cm2) onto tissue culture flasks and Expanded at 378 C and 5% CO2, changing the culture medium every 7 days. Cells were passed to a new culture flask (10008 cells=cm2) when cultures reached 90% of confluence. Cells were phenotypically characterized by their capacity to differentiate into chondro-, osteo-, and adipogenic lineages. In addition, hASCs were verified by staining with specific surface markers. hASCs were positive for HLA-I, CD90, and CD105, and negative for HLA-II, CD40, CD80, CD86, and CD34. A pool from six healthy donors (three men and three women, aged between 35 and 47) was used in the study. Cells were used at passages 4-6.

In some embodiments the ASCs (i) do not express markers specific from APCs; (ii) do not express IDO constitutively (iii) do not significantly express MHC II constitutively. Typically expression of IDO or MHC II may be induced by stimulation with IFN-γ.

In some embodiments the ASCs may express one or more (e.g. two or more, three or more, four or more, five or more, six or more, seven or more, eight or more, nine or more, or ten or more (e.g. up to 13)) of the markers CD9, CD10, CD13, CD29, CD44, CD49A, CD51, CD54, CD55, CD58, CD59, CD90 and CD105. For example, the ASCs may express one or more (e.g. two, three or all) of the markers CD29, CD59, CD90 and CD105, e.g. CD59 and/or CD90.

In some embodiments the MSCs may not express one or more (e.g. two or more, three or more, four or more, five or more, six or more, seven or more, eight or more, nine or more, or ten or more (e.g. up to 15)) of the markers Factor VIII, alpha-actin, desmin, S-100, keratin, CD11b, CD11c, CD14, CD45, HLAII, CD31, CD34, CD45, STRO-1 and CD133, e.g. the MSCs do not express one or more (e.g. two, three or all) of the markers CD34, CD45, CD31 and CD14, e.g. CD31 and/or CD34.

In one embodiment, provided is an adipose tissue-derived stromal stem cell-containing composition, wherein at least about 50%, at least about 60%, at least about 70%, at least about 80%, at least about 85%, at least about 90%, at least about 95% or typically at least about 96%, 97%, 98% or 99% of the stem cells express the CD9, CD10, CD13, CD29, CD44, CD49A, CD51, CD54, CD55, CD58, CD59, CD90 and/or CD105 markers. In certain embodiments of the adipose tissue-derived stromal stem cell-containing compositions, fewer than about 15%, about 10%, about 5%, and typically about 4%, 3%, 2% or 1% of the stem cells express the CD34, CD11b, CD14, CD15, CD16, CD31, CD34, CD45, CD49f, CD102, CD104, CD106 and/or CD133 markers.

In another embodiment, provided is an adipose tissue-derived stromal stem cell-containing composition, wherein at least about 50%, at least about 60%, at least about 70%, at least about 80%, at least about 85%, at least about 90%, at least about 95% or typically at least about 96%, 97%, 98% or 99% of the stem cells express the c-Kit, vimentin and/or CD90 markers. In certain embodiments of the adipose tissue-derived stromal stem cell-containing compositions, fewer than about 15%, about 10%, about 5%, and typically about 4%, 3%, 2% or 1% of the stem cells express the CD34, Factor VIII, alpha-actin, desmin, S-100 and/or keratin markers. Also provided is an adipose tissue-derived stromal stem cell population that express the c-Kit, vimentin and CD90 markers and does not express the CD34, Factor VIII, alpha-actin, desmin, S-100 and keratin markers.

The phenotypic characterization of a cell population by surface markers can be performed either by individual staining of the cells (flow cytometry) or by making histological cuts of the population in situ, done in accordance with normal methods. The determination of the profile of expression of surface markers by antibodies, immunophenotype characterization, may be direct, using a labeled antibody or indirect, using a second labeled antibody against the primary specific antibody of the cell marker, thus achieving signal amplification. On the other hand, the presence or absence of binding to the antibody may be determined by different methods that include but are not limited to immunofluorescence microscopy and radiography. Similarly, it is possible to carry out the monitoring of the levels of binding of the antibody by flow cytometry, a technique that allows the levels of fluorochrome to be correlated with the quantity of antigens present on the cell surface bound specifically to the labeled antibodies. The differential expression of a series of surface markers on a cell population provides a method for identification and isolation of said population. Accordingly, FACS (Fluorescence Activated Cell Sorting) may typically be used.

In certain embodiments, the adipose tissue-derived stromal stem cell-containing compositions are suspensions of adipose tissue-derived stromal stem cells in various solutions or materials, e.g. for use as pharmaceuticals or biomaterials, as described in more detail below. In one embodiment, the cellular composition comprises a suspension of the subject adipose tissue-derived stromal stem cells in Ringer's solution and HSA. In another embodiment, the cellular composition comprises a suspension of the subject adipose tissue-derived stromal stem cells in a material, such as a polymer, glue, gel, etc. Such suspensions may be prepared, for example, by sedimenting out the subject adipose tissue-derived stromal stem cells from the culture medium and resuspending them in the desired solution or material. The cells may be sedimented and/or changed out of the culture medium, for example, by centrifugation, filtration, ultrafiltration, etc.

The concentration of the subject adipose tissue-derived stromal stem cells in the subject adipose tissue-derived stromal stem cell-containing compositions may be at least about $5\times10^6$ cells/mL, at least about $10\times10^6$ cells/mL, at least about $20\times10^6$ cells/mL, at least about $30\times10^6$ cells/mL, or at least about $40\times10^6$ cells/mL. Typically the concentration between about $1\times10^6$ cells/mL and $1\times10'$ cells/mL, e.g. between about between about $5\times10^6$ cells/mL and $1\times10^7$ cells/mL. In the clinical trial reported in the Examples, the eASCs were administered at a concentration of 5 million cells/mL.

Accordingly, another aspect of the present invention pertains to the progeny of the subject adipose tissue-derived stromal stem cells, e.g. those cells which have been derived from the adipose tissue-derived stromal stem cells. Such progeny can include subsequent generations of adipose tissue-derived stromal stem cells, as well as lineage committed cells generated by inducing differentiation of the subject adipose tissue-derived stromal stem cells after their isolation from the explant, e.g., induced in vitro. In certain embodiments, the progeny cells are obtained after about 2, about 3, about 4, about 5, about 6, about 7, about 8, about 9, or about 10 passages from the parental population. However, the progeny cells may be obtained after any number of passages from the parental population.

In certain embodiments, the adipose tissue-derived stromal stem cell-containing compositions of the invention will be provided as part of a pharmaceutical preparation, e.g., a sterile, free of the presence of unwanted virus, bacteria and other pathogens, as well as pyrogen-free preparation. That is, for human administration, the subject compositions should meet sterility, pyrogenicity as well as general safety and purity standards as required by FDA Office of Biologics standards.

The expanded adipose tissue-derived stromal stem cells are allogeneic with respect to the transplantation host. Because of difficulties in obtaining sufficient autologous stem cells, adipose tissue-derived stromal stem cell from allogeneic donor constitute a valuable alternative source of stem cells for therapeutic use. It is known in the art that bone marrow stromal stem cells and adipose tissue-derived stromal cells did not provoke a response of allogeneic lymphocytes in vitro and consequently, allogeneic adipose tissue-derived stromal stem cells derived from a donor could be used for any patient, irrespective of MHC incompatibility.

Methods of administering the adipose tissue-derived stromal stem cell-containing compositions to subjects, particularly human subjects, which are described in detail herein, include injection or implantation of the cells into target sites in the subjects, the cells can be inserted into a delivery device which facilitates introduction by, injection or implantation, of the cells into the subjects. Such delivery devices include tubes, e.g., catheters, for injecting cells and fluids into the body of a recipient subject. In a preferred embodiment, the tubes additionally have a needle, e.g., a syringe, through which the adipose tissue-derived stromal stem cell-containing compositions can be introduced into the subject at a desired location. The adipose tissue-derived stromal stem cell-containing compositions can be inserted into such a delivery device, e.g., a syringe, in different forms. For example, the adipose tissue-derived stromal stem cell-containing compositions include compositions of adipose tissue-derived stromal stem cells that are suspended in a solution or embedded in a support matrix when contained in such a delivery device.

Pharmaceutically acceptable carriers and diluents include saline, aqueous buffer solutions, solvents and/or dispersion media. The use of such carriers and diluents is well known in the art. The solution is typically sterile and fluid to the extent that easy syringability exists. Typically, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions that are adipose tissue-derived stromal stem cell compositions of the invention can be prepared by incorporating adipose tissue-derived stromal stem cells as described herein in a pharmaceutically acceptable carrier or diluent and, as required, other ingredients enumerated above, followed by filtered sterilization.

Some examples of materials and solutions which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

In certain embodiments, the adipose tissue-derived stromal stem cell-containing compositions further comprise an adhesive. In certain embodiments, the adhesive is a fibrin-based adhesive, such as a fibrin gel or fibrin glue or fibrin-based polymer or adhesive, or other tissue adhesive or surgical glue, such as, for example cyanoacrylate, collagen, thrombin, and polyethylene glycol. Other materials that may be used include but are not limited to calcium alginate, agarose, types I, II, IV or other collagen isoform, poly-lactic/poly-glycolic acid, hyaluronate derivatives or other materials (Perka C. et al. (2000) J. Biomed. Mater. Res. 49:305-311; Sechriest V F. et al. (2000) J. Biomed. Mater. Res. 49:534-541; Chu C R et al. (1995) J. Biomed. Mater. Res. 29:1147-1154; Hendrickson D A et al. (1994) Orthop. Res. 12:485-497). In other embodiments, the adhesive is a liquid bandage, wherein adipose tissue-derived stromal stem cell-containing compositions of the method are mixed with the liquid bandage material. A "liquid bandage" is a solution comprising a compound, e.g. a polymeric material, which is applied to a wound with a spray or a brush, followed by removing the solvent by vaporization to provide a protective film on the wound.

The adipose tissue-derived stromal stem cell-containing compositions of the invention may also be used to coat a support, e.g. a medical device. For example, the support may be a suture or thread.

The support may be coated with cells in any way as known to one of skill in the art, e.g. by soaking, spraying, painting, imprinting, etc.

In one embodiment, the support is a suture, staple, absorbable thread, non-absorbable thread, natural thread, synthetic thread, monofilament thread or multifilament thread (also called braids). Preferred methods of preparing sutures and other supports used to close wounds coated with adipose tissue-derived stromal stem cells are disclosed in U.S. patent application Ser. No. 11/056,241 "Biomaterial for Suturing", filed Feb. 14, 2005, which application is incorporated by reference in its entirety. The adipose tissue-derived stromal stem cell-containing compositions disclosed herein represent novel compositions that may be used with the methods disclosed in U.S. patent application Ser. No. 11/056,241.

Further, in any of the adipose-tissue derived stromal stem cell-containing compositions, at least one therapeutic agent may be incorporated into the composition (although not required and can optionally be excluded). For example, a composition may contain an analgesic, to aid in treating inflammation or pain at the site of the fistula, or an anti-infective agent to prevent infection of the site treated with the composition.

More specifically, non-limiting examples of useful therapeutic agents include the following therapeutic categories: analgesics, such as nonsteroidal anti-inflammatory drugs, opiate agonists and salicylates; anti-infective agents, such as antihelmintics, antianaerobics, antibiotics, aminoglycoside antibiotics, antifungal antibiotics, cephalosporin antibiotics, macrolide antibiotics, miscellaneous ß-lactam antibiotics, penicillin antibiotics, quinolone antibiotics, sulfonamide antibiotics, tetracycline antibiotics, antimycobacterials, anti-tuberculosis antimycobacterials, antiprotozoals, antimalarial antiprotozoals, antiviral agents, anti-retroviral agents, scabicides, anti-inflammatory agents, corticosteroid anti-inflammatory agents, antipruritics/local anesthetics, topical anti-infectives, antifungal topical anti-infectives, antiviral topical anti-infectives; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agents, digestants, emetics, laxatives and stool softeners, and pro-kinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hormones and hormone modifiers, such as abortifacients, adrenal agents, corticosteroid adrenal agents, androgens, anti-androgens, immunobiologic agents, such as immunoglobulins, immunosuppressives, toxoids, and vaccines; local anesthetics, such as amide local anesthetics and ester local anesthetics; musculoskeletal agents, such as antigout anti-inflammatory agents, corticosteroid anti-inflammatory agents, gold compound anti-inflammatory agents, immunosuppressive anti-inflammatory agents, nonsteroidal anti-inflammatory drugs (NSAIDs), salicylate anti-inflammatory agents, minerals; and vitamins, such as vitamin A, vitamin B, vitamin C, vitamin D, vitamin E, and vitamin K.

Preferred classes of useful therapeutic agents from the above categories include: (1) analgesics in general, such as lidocaine or derivatives thereof, and nonsteroidal anti-inflammatory drugs (NSAIDs) analgesics, including diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) $H_1$-blocker antihistamines, such as clemastine and terfenadine; (5) anti-infective agents, such as mupirocin; (6) antianaerobic anti-infectives, such as chloramphenicol and clindamycin; (7) antifungal antibiotic anti-infectives, such as amphotericin b, clotrimazole, fluconazole, and ketoconazole; (8) macrolide antibiotic anti-infectives, such as azithromycin and erythromycin; (9) miscellaneous ß-lactam antibiotic anti-infectives, such as aztreonam and imipenem; (10) penicillin antibiotic anti-infectives, such as nafcillin, oxacillin, penicillin G, and penicillin V; (11) quinolone antibiotic anti-infectives, such as ciprofloxacin and norfloxacin; (12) tetracycline antibiotic anti-infectives, such as doxycycline, minocycline, and tetracycline; (13) antituberculosis antimycobacterial anti-infectives such as isoniazid (INH), and rifampin; (14) antiprotozoal anti-infectives, such as atovaquone and dapsone; (15) antimalarial antiprotozoal anti-infectives, such as chloroquine and pyrimethamine; (16) anti-retroviral anti-infectives, such as ritonavir and zidovudine; (17) antiviral anti-infective agents, such as acyclovir, ganciclovir, interferon alfa, and rimantadine; (18) antifungal topical anti-infectives, such as amphotericin B, clotrimazole, miconazole, and nystatin; (19) antiviral topical anti-infectives, such as acyclovir; (20) electrolytic and renal agents, such as lactulose; (21) loop diuretics, such as furosemide; (22) potassium-sparing diuretics, such as triamterene; (23) thiazide diuretics, such as hydrochlorothiazide (HCTZ); (24) uricosuric agents, such as probenecid; (25) enzymes such as RNase and DNase; (26) antiemetics, such as prochlorperazine; (27) salicylate gastrointestinal anti-inflammatory agents, such as sulfasalazine; (28) gastric acid-pump inhibitor anti-ulcer agents, such as omeprazole; (29) $H_2$-blocker anti-ulcer agents, such as cimetidine, famotidine, nizatidine, and ranitidine; (30) digestants, such as pancrelipase; (31) prokinetic agents, such as erythromycin; (32) ester local anesthetics, such as benzocaine and procaine; (33) musculoskeletal corticosteroid anti-inflammatory agents, such as beclomethasone, betamethasone, cortisone, dexamethasone, hydrocortisone, and prednisone; (34) musculoskeletal anti-inflammatory immunosuppressives, such as azathioprine, cyclophosphamide, and methotrexate; (35) musculoskeletal nonsteroidal anti-inflammatory drugs (NSAIDs), such as diclofenac, ibuprofen, ketoprofen, ketorlac, and naproxen; (36) minerals, such as iron, calcium, and magnesium; (37) vitamin B compounds, such as cyanocobalamin (vitamin $B_{12}$) and niacin (vitamin $B_3$); (38) vitamin C compounds, such as ascorbic acid; and (39) vitamin D compounds, such as calcitriol.

In certain embodiments, the therapeutic agent may be a growth factor or other molecule that affects cell differentiation and/or proliferation. Growth factors that induce final differentiation states are well-known in the art, and may be selected from any such factor that has been shown to induce a final differentiation state. Growth factors for use in methods described herein may, in certain embodiments, be variants or fragments of a naturally-occurring growth factor. For example, a variant may be generated by making conservative amino acid changes and testing the resulting variant in one of the functional assays described above or another functional assay known in the art. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As those skilled in the art will appreciate, variants or fragments of polypeptide growth factors can be generated using conventional techniques, such as mutagenesis, including creating discrete point mutation(s), or by truncation. For instance, mutation can give rise to variants which retain substantially the same, or merely a subset, of the biological activity of a polypeptide growth factor from which it was derived.

3. Methods of Preparing Adipose Tissue-Derived Stromal Stem Cell-Containing Compositions Methods for the isolation and culture of ASCs to provide eASCs and cell populations of the invention, and compositions comprising cell populations of the invention are known in the art. Typically methods for the preparation of compositions comprising cell populations comprise the following steps:

(i) isolation of ASCs from the stromal fraction of adipose tissue and selection by adherence to a suitable surface e.g. plastic (ii) expansion of ASCs to provide cell populations of the invention comprising eASCs.

Optionally the cell populations of the invention may be cryopreserved during and/or subsequent to the expansion step (ii). Optionally the phenotype of the cell populations of the invention may be assessed during and/or subsequent to the expansion step (ii). Optionally the cell populations of the invention may be isolated subsequent to the expansion step (ii) and resuspended in a pharmaceutically acceptable carrier and/or diluents.

ASCs can be obtained by any means standard in the art. Typically said cells are obtained disassociating the cells from the source tissue (e.g. lipoaspirate or adipose tissue), typically by treating the tissue with a digestive enzyme such as collagenase. The digested tissue matter is then typically filtered through a filter of between about 20 microns to 1 mm. The cells are then isolated (typically by centrifugation) and cultured on an adherent surface (typically tissue culture plates or flasks). Such methods are known in the art and e.g. as disclosed in U.S. Pat. No. 6,777,231. According to this methodology, lipoaspirates are obtained from adipose tissue and the cells derived therefrom. In the course of this methodology, the cells may be washed to remove contaminating debris and red blood cells, preferably with PBS. The cells are digested with collagenase (e.g. at 37° C. for 30 minutes, 0.075% collagenase; Type I, Invitrogen, Carlsbad, Calif.) in PBS. To eliminate remaining red blood cells, the digested sample can be washed (e.g. with 10% fetal bovine serum), treated with 160 mmol/L ClNH4, and finally suspended in DMEM complete medium (DMEM containing 10% FBS, 2 mmol/L glutamine and 1% penicillin/streptomycin). The cells can be filtered through a 40-µm nylon mesh.

The cells are cultured in a suitable tissue culture vessel, comprising a surface suitable for the adherence of ASCs e.g. plastic. Non-adherent cells are removed e.g. by washing in a suitable buffer, to provide an isolated population of adherent stromal cells (e.g. ASC). Cells isolated in this way can be seeded (preferably 2-3×104 cells/cm2) onto tissue culture flasks and expanded at 37° C. and 5% CO2, changing the culture medium every 3-4 days. Cells are preferably deatxhed from the adherent surface (e.g. by means of trypsin) and passed ("passaged") to a new culture flask (1,000 cells/cm2) when cultures reach around 90% of confluence.

Cell isolation is preferably carried out under sterile or GMP conditions.

In one embodiment, a method comprises: (a) collecting adipose tissue from a subject; (b) obtaining a cell suspension by enzymatic digestion; (c) sedimenting the cell suspension and resuspending the cells in a culture medium; (d) culturing of the cells for at least about 10 days; and (g) expanding the cells for at least two culture passages. The adipose tissue-derived stromal stem cells are alloegenic, i.e. not isolated from the adipose tissue of the subject into which the final adipose tissue-derived stromal stem cell-containing composition is to be introduced.

In certain embodiments, the cells are cultured for at least about 15, at least about 20 days, at least about 25 days, or at least about 30 days. Typically the expansion of cells in culture improves the homogeneity of the cell phenotype in the cell population, such that a substantially pure or homogenous population is obtained.

In certain embodiments, the cells are expanded in culture for at least three culture passages or "passaged at least three times." In other embodiments, the cells are passaged at least four times, at least five times, at least six times, at least seven times, at least eight times, at least nine times, or at least ten times. It is preferable that cells are passaged more than three times to improve the homogeneity of the cell phenotype in the cell population. Indeed, the cells may be expanded in culture indefinitely so long as the homogeneity of the cell phenotype is improved and differential capacity is maintained.

In certain embodiments, the cells are multiplied in culture for at least three population doublings. In certain embodiments, the cells are expanded in culture for at least four, five, six, seven, eight, nine, ten, 15 or 20 population doublings. In certain embodiments, the cells are expanded in culture for less than seven, eight, nine, ten, 15 or 20 population doublings. In certain embodiments, the cells are expanded in culture for between about 5 and 10 population doublings. In certain embodiments, the cells are expanded in culture for between about 10 and 15 population doublings.

In certain embodiments, the cells are expanded in culture for between about 15 and 20 population doublings, for example about 16 population doublings.

Cells may be cultured by any technique known in the art for the culturing of stem cells. A discussion of various culture techniques, as well as their scale-up, may be found in Freshney, R. I., *Culture of Animal Cells: A Manual of Basic Technique*, 4th Edition, Wiley-Liss 2000. Cells may be expanded using culture flasks or bioreactors suitable for large-scale expansion. Bioreactors suitable for the large-scale expansion of mesenchymal stromal cells are commercially available and may include both 2D (i.e. substantially planar) and 3D expansion bioreactors. Examples of such bioreactors include, but are not limited to, a plug flow bioreactor, a perfusion bioreactor, a continuous stirred tank bioreactor, a stationary-bed bioreactor. In certain embodiments, the cells are cultured by monolayer culture. In one embodiment, the cells are cultured and passaged as described in Example A below.

Any medium capable of supporting stromal cells in tissue culture may be used. Media formulations that will support the growth of fibroblasts include, but are not limited to, Dulbecco's Modified Eagle's Medium (DMEM), alpha modified Minimal Essential Medium (alpha.MEM), and Roswell Park Memorial Institute Media 1640 (RPMI Media 1640) and the like. Typically, 0 to 20% Fetal Bovine Serum (FBS) or 1-20% horse serum will be added to the above media in order to support the growth of stromal cells and/or chondrocytes. However, a defined medium could be used if the necessary growth factors, cytokines, and hormones in FBS for stromal cells and chondrocytes are identified and provided at appropriate concentrations in the growth medium. Media useful in the methods of the invention may contain one or more compounds of interest, including, but not limited to antibiotics mitogenic or differentiative compounds for stromal cells. The cells will be grown at temperatures between 31° C. to 37° C. in a humidified incubator. The carbon dioxide content will be maintained between 2% to 10% and the oxygen content between 1% and 22%. Cells may remain in this environment for periods of up to 4 weeks.

Antibiotics which can supplemented into the medium include, but are not limited to penicillin and streptomycin. The concentration of penicillin in the chemically defined culture medium is about 10 to about 200 units per ml. The concentration of streptomycin in the chemically defined culture medium is about 10 to about 200 ug/ml.

The adipose tissue derived stromal stem cells may be stably or transiently transfected or transduced with a nucleic acid of interest using a plasmid, viral or alternative vector strategy. Nucleic acids of interest include, but are not limited to, those encoding gene products which enhance the production of extracellular matrix components found in the tissue type to be repaired, e.g. intestinal wall or vaginal wall.

The transduction of viral vectors carrying regulatory genes into the stromal stem cells can be performed with viral vectors (adenovirus, retrovirus, adeno-associated virus, or other vector) purified by cesium chloride banding or other method at a multiplicity of infection (viral units:cell) of between 10:1 to 2000:1. Cells will be exposed to the virus in serum free or serum-containing medium in the absence or presence of a cationic detergent such as polyethyleneimine or Lipofectamine™ for a period of 1 hour to 24 hours (Byk T. et al. (1998) Human Gene Therapy 9:2493-2502; Sommer B. et al. (1999) Calcif. Tissue Int. 64:45-49).

Other suitable methods for transferring vectors or plasmids into stem cells include lipid/DNA complexes, such as those described in U.S. Pat. Nos. 5,578,475; 5,627,175; 5,705,308; 5,744,335; 5,976,567; 6,020,202; and 6,051,429. Suitable reagents include lipofectamine, a 3:1 (w/w) liposome formulation of the poly-cationic lipid 2,3-dioleyloxy-N-[2(sperminecarbox-amido)ethyl]-N,N-dimethyl-1-propanaminium trifluoroacetate (DOSPA) (Chemical Abstracts Registry name: N-[2-(2,5-bis[3-aminopropyl)amino]-1- oxpentyl}amino)ethyl]-N,N-dimethyl-2,3-bis(9-octadecenyloxy)-1-propanamin-ium trifluoroacetate), and the neutral lipid dioleoyl phosphatidylethanolamine (DOPE) in membrane filtered water. Exemplary is the formulation Lipofectamine 2000™ (available from Gibco/Life Technologies #11668019). Other reagents include: FuGENE™ 6 Transfection Reagent (a blend of lipids in non-liposomal form and other compounds in 80% ethanol, obtainable from Roche Diagnostics Corp. #1814443); and LipoTAXI™ transfection reagent (a lipid formulation from Invitrogen Corp., #204110). Transfection of stem cells can be performed by electroporation, e.g., as described in M. L. Roach and J. D. McNeish (2002) Methods in Mol. Biol. 185:1. Suitable viral vector systems for producing stem cells with stable genetic alterations may be based on adenoviruses and retroviruses, and may be prepared using commercially available virus components.

The transfection of plasmid vectors carrying regulatory genes into the stem stromal cells can be introduced into the cells in monolayer cultures by use of calcium phosphate DNA precipitation or cationic detergent methods (Lipofectamine™, DOTAP) or in three dimensional cultures by incorporation of the plasmid DNA vectors directly into the biocompatible polymer (Bonadio J. et al. (1999) Nat. Med. 5:753-759).

For the tracking and detection of functional proteins encoded by these genes, the viral or plasmid DNA vectors will contain a readily detectable marker gene, such as the green fluorescent protein or beta-galactosidase enzyme, both of which can be tracked by histochemical means.

4. Treating Complex Perianal Fistulae

The invention concerns the treatment of complex perianal fistulae in Crohn's disease patients, using expanded allogeneic adipose tissue-derived stromal stem cells. The adipose tissue-derived stromal stem cells typically comprise an adipose tissue-derived stromal stem cell-containing composition described herein, sometimes referred to as "Cx601". However, other preparations of adipose tissue-derived stromal stem cells may be used in the methods described herein, e.g. such as those described in U.S. Pat. Nos. 6,777,231 and 6,555,374 and U.S. patent application Ser. No. 11/065,461 "Identification and Isolation of Multipotent Cells From Non-Osteochondral Mesenchymal Tissue", filed on Feb. 25, 2005.

The Examples show that allogeneic eASCs are a surprisingly effective therapy for complex perianal fistulae in Crohn's Disease patients, whereby a single adminstration is able to provide a rapid and sustained therapeutic effect even in the most difficult to treat, very complex fistulae that have not responded to previous treatments. For example, benefit is typically seen by around 6 weeks, and which benefit is typically sustained through to 24 weeks from therapy.

In one embodiment, a method of treating a complex refractory perianal fistula in a Crohn's disease patient comprises injecting about 120 million expanded allogeneic adipose tissue-derived stromal stem cells intralesionally, into all tracts of the fistula. For the avoidance of doubt, in this embodiment 120 million cells are administered to the patient in a single procedure, with each fistula tract receiving at least a proportion of this dosage. Approximately half of the dose is injected into the tissue surrounding the internal opening or openings. The other half is injected into the fistula walls (no deeper than 2 mm) all along the fistula tract(s), making several micro-blebs. The data in the Examples show that this single adminstration is able to provide combined remission within 24 weeks or less, even within around 6 weeks or within around 8 weeks. Accordingly, in one embodiment, the treatment consists of this single intralesional adminstration of 120 million eASCs.

The intraesional injection is typically carried out as in the exemplified clinical trial, whereby the cell suspension is injected through the internal opening(s) (with the syringe entering through the anus) and through the fistula tract walls (with the syringe entering through the external opening of the fistula).

The patient may be male or female. The patient is typically an adult.

In one embodiment, any setons that may be present are first removed. Typically, the fistula is curetted prior to administration of the eASCs. Internal openings may optionally be sutured. The eASCs are then administered with a fine, long needle. As noted above, approximately half of the dose is injected into the tissue surrounding the sutured internal opening(s). The other half is injected into the fistula walls (no deeper than 2 mm) all along the fistula tract(s), making several micro-blebs.

Prior to therapy according to the invention, a pelvic MRI scan may be performed at screening to guide the surgical procedures. Patients may also undergo fistula curettage and seton placement as clinically indicated ≥2 weeks before investigational product administration (FIG. 1). If a seton was placed, it is withdrawn immediately before investigational product administration.

The patient to be treated has Crohn's disease, typically luminal Crohn's disease. Typically the patient has had non-active or mildly active luminal Crohn's disease, for example as defined by a Crohn's Disease Activity Index (CDAI) of ≤220[424]. The patient may have had Crohn's disease for at least 6 months.

The patient has at least one complex perianal fistula. In one embodiment, the patient does not have a rectovaginal fistula, rectal stenosis, anal stenosis, active severe proctitis (defined by the presence of superficial or deep ulcers), diverting stomas, or an abscess or collections >2 cm which were not resolved by the surgical preparation procedure.

Patients are refractory to at least one previous drug therapy. The previous therapy may be a small molecule drug or biological medicinal product. Typically the patient has received said treatment for at least about 4, 6, 12, 18, 24 or 36 weeks and still presents symptoms of active disease. In other words, even after treatment for at least about 4, 6, 12, 18, 24 or 36 weeks, the severity of the fistula is not ameliorated. The previous therapy may be antibiotic therapy such as ciprofloxacin or metronidazole, immunosuppressant therapy (e.g. a purine analogue such as azathioprine or 6-mercaptopurine, a pyrminidine analogue such as fluorouracil, or a folic acid analogue such as methotraxate), or anti-TNF therapy such as Adalimumab (Humira), Certolizumab (Cimzia), Etanercept (Enbrel), Golimumab (Simponi), or Infliximab (Remicade). Eligible patients are typically refractory (no response) to at least one of the following treatments: after 1 month of antibiotics (e.g. ciprofloxacin, metronidazole); and/or after 3 months of immunosuppressants (e.g. azathioprine, 6-mercaptopurine); and/or of induction or maintenance of anti-TNF therapies (e.g. infliximab, etanercept, adalimumab, certolizumab, golimumab) at a stable dose.

In one embodiment the patient is treatment refractory to an immunosuppressant (e.g. azathioprine, 6-mercaptopurine) and a TNF-α inhibitor (e.g. infliximab or adalimumab).

A typical patient therefore has non-active luminal Crohn's disease (CDAI≤220) diagnosed for at least six months, with a complex perianal fistula having 1 or 2 internal openings and 2 or 3 external openings, that has shown inadequate response to one or more of antibiotics, immunosuppressants or anti-TNF therapies. A fistula with 1 or 2 internal openings and 3 external openings is highly complex and until now has been very difficult to treat. In a further embodiment, at the time of the treatment according to the invention, the patient is receiving (a) no anti-TNF therapy and no immunosuppressant therapy, or (b) both an anti-TNF therapy and an immunosuppressant therapy. It is especially suprising that eASCs are able to improve significantly the combined remisison (at week 24) in patients receiving both anti-TNF and immunosuppression therapy, which are the best currently available therapies (see FIG. 3C).

The complex perianal fistula has at least two external openings, for example 3 or more external openings. Some fistulas may have 4 or 5 external openings.

The complex perianal fistula typically has multiple tracts, at least two internal openings, or three external openings. The fistula may optionally comprise two or three of these features, for example: multiple tracts and at least two internal openings; multiple tracts and three external openings; at least two internal openings and three external openings; or multiple tracts, at least two internal openings and three external openings. In one embodiment, the complex perianal fistula contains no more than two internal openings and three external openings, for example the fistula consists of 1 or 2 internal openings and 2 or 3 external openings (e.g. 1IO/2EO, 1IO/3EO, 2IO/2EO, or 2IO/3EO).

Following eASC administration, patients may optionally be treated with antibiotics for no more than 4 weeks Immunosuppressants and anti-TNFs may be maintained at stable doses throughout the treatment, e.g. until response, clinical remission or combined remission.

Patients who had not received prior treatment for perianal fistulizing Crohn's disease, including antibiotics, and those who underwent previous surgery for the active fistula other than drainage or seton placement are typically excluded. Patients are typically not eligible for treatment if they have received glucocorticosteroids within the 4 weeks immediately prior to eASC treatment. A steroid course may be permitted to treat flares of luminal disease during follow-up with a starting dose of 40 mg taped over a maximum of 12 weeks.

In certain embodiments, e.g., wherein the first delivery of cells is insufficient, the method may further comprise a further administration of the eASCS. This further administration may comprise: (c) delivering a second dose of at least about $20 \times 10^6$ cells, at least about $30 \times 10^6$, or at least about $40 \times 10^6$ adipose tissue-derived stromal stem cells, for example about 120 million cells, e.g., in an adipose tissue-derived stromal stem cell-containing composition of the invention, to the (optionally closed sutured) internal hole and the fistula walls.

In some embodiments, a method of treating a refractory complex perianal fistula in a subject comprises: (a) closing the internal hole with a suture that comprises allogeneic eASCs. Such sutures coated with cells in the subject adipose tissue-derived stromal stem cell-containing compositions are described in detail in U.S. patent application Ser. No. 11/056,241, filed on Feb. 14, 2005, which is incorporated herein by reference.

The methods may in some embodiments further comprise: deep scraping of at least one fistula tract; and/or filling said fistula tract with a material. In certain embodiments, the method may further comprise delivering at least about $10 \times 10^6$ adipose tissue-derived stromal stem cells, e.g., from a subject cellular composition, to the material. Typically, the material is a fibrin-based polymer or adhesive, such as a fibrin glue or gel. In certain embodiments, the dose of at least about $10 \times 10^6$ adipose tissue-derived stromal stem cells is already encompassed within the material, e.g., such that the material comprises the adipose tissue-derived stem cell containing-composition.

In a further embodiment, a method of treating a fistula in a subject comprises:
  (i) deep scraping of at least one fistula tract
  (ii) closing the internal hole of the scraped tract with a suture
  (iii) delivering about 120 million alloegeneic expanded adipose tissue-derived stromal stem cells to an (optionally closed sutured) internal opening and the fistula walls e.g., in an adipose tissue-derived stromal stem cell-containing composition of the invention.

A further administration of cells is not required and may optionally be excluded. However, in certain embodiments the method may further comprise:
  (iv) delivering a second dose of at least about $20 \times 10^6$ cells, at least about $30 \times 10^6$, or at least about $40 \times 10^6$ adipose tissue-derived stromal stem cells, e.g. about 120 million eASCs, typically to a closed sutured internal opening, e.g., in an adipose tissue-derived stromal stem cell-containing composition of the invention.

Step (i) is typically carried out by deep scraping all fistula tracts to be treated for example, a curettage needle is introduced in the fistula tract, and an induced bleeding is produced by scraping the fistula walls in order to obtain natural fibrin which will fill the fistula tract. Previous clinical studies by the inventors suggest that the natural fibrin produced by this scraping method is a preferred option compared with the use of artificial fibrin sealants, therefore in a preferred embodiment of the method of the invention the fistular tracts to be treated are not filled with such material.

Step (iv) is carried out by local delivery of the cells, for example an adipose tissue-derived stromal stem cell-containing composition, by injection into the fistula walls along the fistula tract. For example, multiple injections of 10 million cells along 3 cm of fistula tract.

The fistula may be accessed for surgical repair via any method known in the art, e.g., via incision, catheter, etc.

The methods described above may further comprise administering a therapeutic agent to the subject being treated, e.g. systemically or locally at the site of suturing. In certain embodiments, the adipose tissue-derived stromal stem cells are formulated in an adipose tissue-derived stromal stem cell-containing composition which contains a therapeutic agent, as described above. In other embodiments, the therapeutic agent is administered separately, e.g. simultaneously with the methods, before the method is performed, or after the method is performed. In some embodiments, the therapeutic agent is administered to the subject before, during and after the methods are performed on the subject. Exemplary therapeutic agents are described above. In preferred embodiments, therapeutic agents for the treatment of Crohn's disease are administered to the subject. Exemplary Crohn's disease therapeutic agents are anti-inflammatory agents such as agents comprising mesalamine, immunosuppressive agents such as 6-mercaptopurine and azathioprine; biological agents such as infliximab (Remicade®), antibiotics, and antidiarrheal agents such as diphenoxylate, loperamide, and codeine.

Supportive treatment may be required. For example, immunosuppressants may be administered before, during and/or after treatment to prevent GVHD, according to methods known in the art. Prior to administration, the cells may also be modified to suppress an immune reaction from the subject to the cells or vice-versa, according to methods known in the art.

The dosage of any therapeutic agent will vary depending on the symptoms, age and body weight of the patient, the nature and severity of the disorder to be treated or prevented, the route of administration, and the form of the agent. Any of the subject formulations may be administered in a single dose or in divided doses. Dosages for the therapeutic agents may be readily determined by techniques known to those of skill in the art or as taught herein. Also, mixtures of more than one therapeutic agent may be administered, or multiple therapeutic agents administered in separate compositions.

The precise time of administration and amount of any particular agent that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

The combined remission of the fistula exmplifed herein comprises both clinical and radiological remission. The radiological assessement of remission is typically carried out by MRI, which is a well-known technique. Other imaging techniques may alternatively be used, for example endorectal ultrasonography. These imaging techniques assess the existence of ascesses or collections.

Treatment may be initiated with smaller dosages which are less than the optimum dose of the compound. Thereafter, the dosage may be increased by small increments until the optimum therapeutic effect is attained.

The combined use of several therapeutic agents may reduce the required dosage for any individual component because the onset and duration of effect of the different components may be complimentary. In such combined therapy, the different active agents may be delivered together or separately, and simultaneously or at different times within the day.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. Although compounds that exhibit toxic side effects may be used, care should be taken to design a delivery system that targets the agents to the desired site in order to reduce side effects.

The data obtained from the cell culture assays and animal studies may be used in formulating a range of dosage for use in humans. The dosage of any therapeutic agent or alternatively of any components therein, lies typically within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

5. Clinical Response and Remission

The allogeneic eASCs of the invention are suprisingly effective at treating refractory complex perianal fistulae in Crohn's disease patients. The primary endpoint, Combined Remission at week 24, is statistically met; Cx601 is statistically superior to placebo. Both key secondary endpoints, Clinical Remission and Response at Week 24, meet borderline statistical significance (p=0.064 & p=0.054 in the ITT population; p=0.057 & 0.045 in the mITT population, respectively).

The data indicate that patients receiving a single administration of eASCs have a 30% greater chance of achieving clinical remission than placebo. The data also indicate that patients receiving eASCs have around 35% greater chance of achieving a clinical response, than placebo.

In certain embodiments, clinical remission is achieved within 24 weeks, typically within 18 weeks. Clinical remission may be achieved within 12 weeks, or less, for example within 10 weeks, or within 8 weeks. Clinical remission may optionally be achieved after 6 weeks. The data show that the median time to clinical remission is around 2-fold shorter with Cx601 than placebo (6.7 weeks v 14.6 weeks). Accordingly, in one embodiment clinical remission is achieved within 14 weeks.

In some embodiments, combined remission is achieved within 24 weeks, typically within 18 weeks. Combined remission may optionally be achieved within 12 weeks, or less, for example within 10 weeks, or within 8 weeks. Combined remission may optionally be achieved after 6 weeks.

In certain embodiments, clinical response is achieved in 11 weeks or less. The data show that the median time to clinical response is also around 2-fold shorter than placebo (6.3 weeks v 11.7 weeks). The time to clinical response can in certain embodiments be 10 weeks or less, 9 weeks or less, 8 weeks or less. The time to clinical response may optionally be 7 weeks or less, for example around 6 weeks.

These results are particularly surprising when it is noted that these improvements are observed after a single administration of the eASCs.

The Perianal Disease Activitiy Index "PDAI" comprises five categories: discharge, pain, restriction of sexual activity, type of perianal disease and degree of induration. Each category is graded on a five-point scale, ranging from no symptoms (score 0) to severe symptoms (score 4). An improvement in Perianal Disease Activity Index Score is observed to be significantly greater for eASCs than placebo at weeks 6, 12 and 18. Therefore, in certain embodiments, an improvement in PDAI is achieved within 6 weeks, within 12 weeks or within 18 weeks. The improvement in PDAI may optionally be an improvement of greater than 1.5 PDAI points, optionally at least two PDAI points. The improvement in PDAI may optionally be a decrease (improvement) in each of the five components of the index.

6. Kits

In other embodiments, the invention contemplates kits including the adipose tissue-derived stromal stem cell-containing compositions and optionally instructions for their use. Kits comprising the pharmaceutical compositions and biomaterials of the present invention are also within the scope of the invention. Kit components may be packaged for either manual or partially or wholly automated practice of the foregoing methods. Such kits may have a variety of uses, including, for example, therapy, repair, preparation of biomaterials and other applications.

EXEMPLIFICATION

The invention now being generally described, it will be more readily understood by reference to the following examples, which are included merely for purposes of illustration of certain aspects and embodiments of the present invention, and are not intended to limit the invention.

Phase III Clinical Trial

The current study is the first placebo-controlled phase 3 study evaluating the efficacy and safety of Cx601 alone or added on to current medical therapy for treatment-refractory complex perianal fistulas in Crohn's disease patients.

Overall, the results demonstrate that allogeneic eASCs are indicated for the treatment of complex perianal fistula(s) in adult patients with non-active/mildly active luminal Crohn's disease, when fistula(s) have shown an inadequate response to at least one conventional or biologic therapy.

Methods

Study Oversight

This phase 3, randomized, double-blind, parallel-group, placebo-controlled study (NCT01541579; EUDRACT 2011-006064-43) was conducted at 49 medical centers in 7 European countries and Israel from July 2012 to July 2015. The protocol was approved by a central or local ethics committee. All patients gave written informed consent.

The study was designed and implemented by the ADMIRE Steering Committee (see Supplementary Appendix). The sponsor collected the data, which were analyzed by the Department of Biostatistics of Chiltern International, and the sponsor together with the Steering Committee interpreted the data. All the authors had full access to the data, agreed with the decision to submit the final manuscript for publication, and vouch for the accuracy and completeness of the data reported. The manuscript was drafted by the first author and all authors contributed to subsequent drafts.

Patients

Eligible patients were adults aged 18 years or older, had non-active or mildly active luminal Crohn's disease for ≥6 months, defined by a Crohn's Disease Activity Index (CDAI) of ≤220[424], and had complex perianal fistulas (defined as one or more of the following: high inter-, trans-, extra- or supra-sphincteric origin; ≥2 external openings; or associated collections) with a maximum of 2 internal and 3 external openings, which had been draining for ≥6 weeks prior to inclusion. Patients were excluded if they had rectovaginal fistulas, rectal and/or anal stenosis and/or active severe proctitis (defined by the presence of superficial or deep ulcers), diverting stomas, or an abscess or collections >2 cm which were not resolved by the surgical preparation procedure. Eligible patients had to be refractory to at least one of the following treatments documented as no response after 1 month of antibiotics (ciprofloxacin, metronidazole) and/or after 3 months of immunosuppressants (azathioprine, 6-mercaptopurine) and/or of induction or maintenance of anti-TNF therapies at a stable dose. Patients refractory only to antibiotics were to represent <25% of the total population.

Following investigational product administration, patients could be treated with antibiotics for no more than 4 weeks Immunosuppressants and anti-TNFs were maintained at stable doses throughout the study. Initiation or dose increase of these agents were not allowed.

Patients who had not received prior treatment for perianal fistulizing Crohn's disease, including antibiotics, and those who underwent previous surgery for the active fistula other than drainage or seton placement were also excluded. Patients were not eligible if they received glucocorticosteroids within the previous 4 weeks. A steroid course was permitted to treat flares of luminal disease during follow-up with a starting dose of 40 mg taped over a maximum of 12 weeks.

Randomization and Treatment

A pelvic MRI scan was performed at screening to guide the surgical procedures and central blind reading evaluated collections. In addition, patients underwent examination under anesthesia, fistula curettage, and seton placement as clinically indicated ≥2 weeks before investigational product administration (FIG. 1). If a seton was placed, it had to be withdrawn immediately before investigational product administration.

Patients were randomly assigned in a 1:1 ratio to Cx601 or placebo after the fistula preparation visit ≥2 weeks before investigational product administration (FIG. 1). Patients were stratified based on concomitant medication at randomization (anti-TNF and/or immunosuppressant or neither). Treatments were assigned using a pre-established randomization list generated by the Department of Biostatistics, Linical.

Patients in the Cx601 arm received a single injection of 120 million Cx601 intralesionally distributed into fistula tracts. Isolation and expansion of Cx601 was performed as previously described.[423] Patients in the placebo arm received an identical volume of saline solution. Study treatments were administered with a fine, long needle after removing seton(s), if present, and curetting fistula. Half of the dose was injected into the tissue surrounding the sutured internal opening(s). The other half was injected into the fistula walls (no deeper than 2 mm) all along the fistula tract(s), making several micro-blebs.

Blinding of treatments was not possible as the cell suspension was clearly different to saline solution. The double-blind study design was maintained by the treatment being administered by an unblinded surgeon and a blinded gastroenterologist and radiologist evaluating the response.

Study Procedures and Follow-Up

Fistula closure was clinically evaluated at weeks 6, 12, 18 and 24 by the investigator examining for the presence of spontaneous drainage and after gentle finger compression at the treated external openings,[412] and was radiologically assessed by blinded, centrally-read pelvic MRI scan at week 24; central readers were provided with figures to identify the treated fistulas, but were blinded to patient data, order of examinations and treatment received. Treatment-emergent adverse events (TEAEs) were evaluated at all study visits. Severity of perianal Crohn's disease was assessed at baseline and all study visits with the Perianal Disease Activity Index (PDAI).[425] Quality of life was assessed with the Inflammatory Bowel Disease Questionnaire (IBDQ)[426] at baseline and week 24 as was CDAI.[424]

Efficacy and Safety Endpoints

The primary endpoint was combined remission at week 24 defined as the clinical assessment of closure of all treated external openings that were draining at baseline, and the absence of collections >2 cm of the treated perianal fistulas in ≥2 of 3 dimensions, confirmed by blinded central MRI reading (Bioclinica GmbH, Munich, Germany). Clinical assessment of closure was defined as absence of draining despite gentle finger compression.[412]

There were two key secondary efficacy endpoints: clinical remission (i.e., closure of all treated external openings that were draining at baseline despite gentle finger compression) and response (i.e., closure of ≥50% of all treated external openings that were draining at baseline) by week 24. Other secondary efficacy endpoints included time to clinical remission, time to response, PDAI, CDAI and IBDQ scores up to week 24.

TEAEs were coded according to the Medical Dictionary for Regulatory Activities version 17.0.

Statistical Analysis

The planned sample size to be screened was 278 patients in order to randomize ≥208 patients (104 to each group). The sample size was sufficient to detect a minimum 25% difference in the percentage of patients with combined remission between Cx601 and placebo (anticipated minimum combined remission rates were 50% for Cx601 and 25% for placebo[48,412,423,427]) with an alpha error of 0.025, and 80% power, and allowed for 20% of patients discontinuing the study.

Efficacy analyses were conducted on the intention to treat (ITT) population which included all randomized patients, the modified ITT (mITT) population which included all randomized patients who received study treatment and had ≥1 post-baseline efficacy assessment, and the per protocol (PP) population which included all treated patients with no major protocol deviations. TEAEs were analyzed in the safety population defined as all patients who received study treatment.

The primary endpoint was analyzed using a stratified Cochran-Mantel-Haenszel test, adjusting for randomization strata (i.e., Crohn's disease treatments at randomization). The primary analysis was done using the ITT population. We also provide results for the mITT population since its definition more closely resembles the ITT population in other randomized clinical trials and provides a more reliable estimate of treatment effects. Missing data were imputed using the last-observation-carried-forward (LOCF) method. A non-response/non-remission was imputed if a post-baseline MRI scan or clinical assessment was not done by week 24. Non-response/non-remission was also imputed if a rescue event took place before week 24. The effects of rescue events and missing data conventions on efficacy were explored in sensitivity analyses of the primary endpoint.

To address the issue of multiplicity, the two key secondary endpoints (clinical remission and response by week 24) were grouped into a short-term family, with a gatekeeping method using Hochberg's testing procedure[428] to control the overall type I error, with the primary efficacy endpoint acting as the gatekeeper. Statistical significance was assessed with a two-sided type I error level of 0.05. No statistical adjustment for multiplicity was made for non-key secondary endpoints. Percentages and treatment differences were expressed with 95% confidence intervals (CI) calculated with a Wald's asymptotic method. Time to clinical remission and response were analyzed with Kaplan-Meier estimates. Safety outcomes were presented with descriptive statistics.

The SAS System v9.1.3 or later was used for the statistical analyses (SAS Institute Inc., Cary, N.C., USA).

Results

Figure 2:
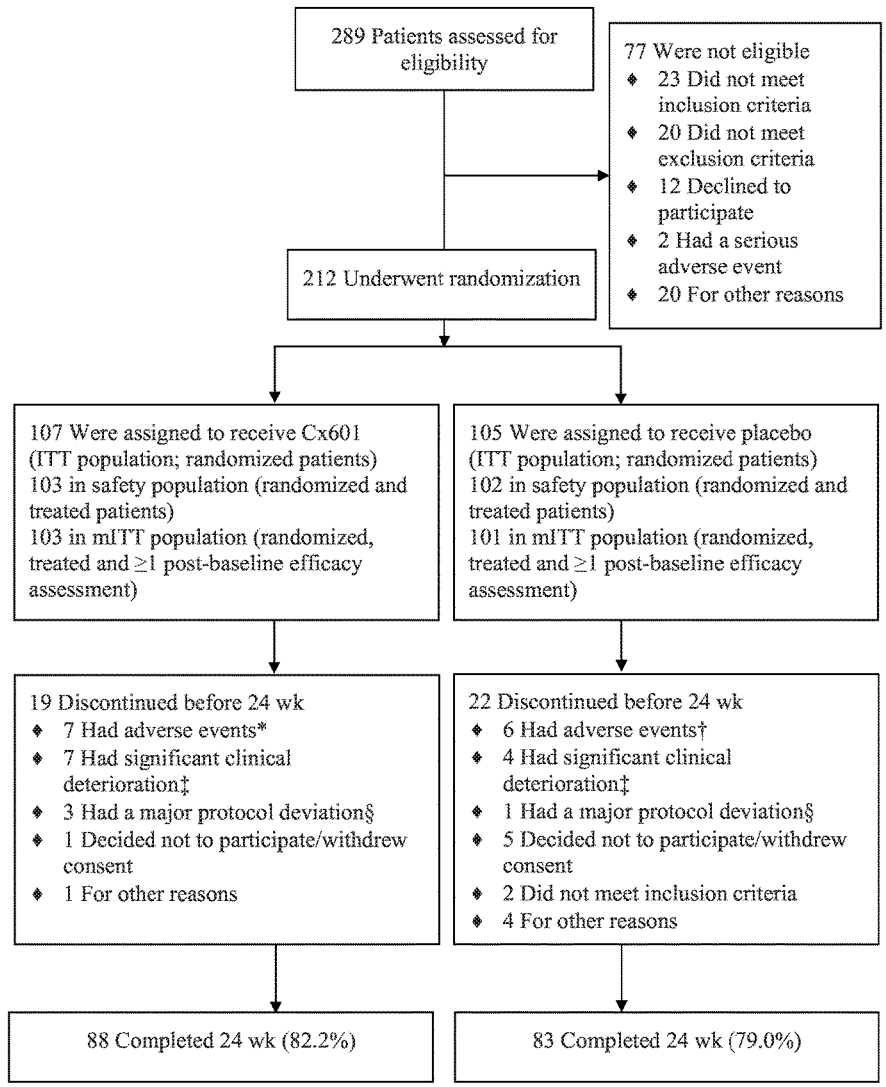
FIG. 2: summarises the Patient disposition. Cx601, allogeneic, expanded, adipose-derived stem cells; ITT, intention to treat; mITT, modified intention to treat; *Deep vein thrombosis, Crohn's flare, intestinal obstruction, Crohn's disease, anal abscess (n=3); †Fistula, proctalgia, anal abscess (n=4); ‡No healing or worsening of symptoms; new course of antibiotics; new surgery in perianal region; § Worsening of Crohn's disease requiring change in therapy.

A total of 289 patients were screened, and of these, 212 were randomized to Cx601 or placebo (FIG. 2). The baseline characteristics of the 2 groups were similar (Table 1). The majority of patients had received ≥1 treatment for Crohn's disease in the past 6 months. A higher proportion of patients in the Cx601 group had multiple tract fistulas compared with the placebo group (46.6% and 30.4%, respectively). A total of 171 patients (80.7%) completed the 24-week follow-up. During the study, 1 patient in the Cx601 group and 4 patients in the placebo group received steroids for flare of Crohn's disease.

Efficacy

Figure 3A:
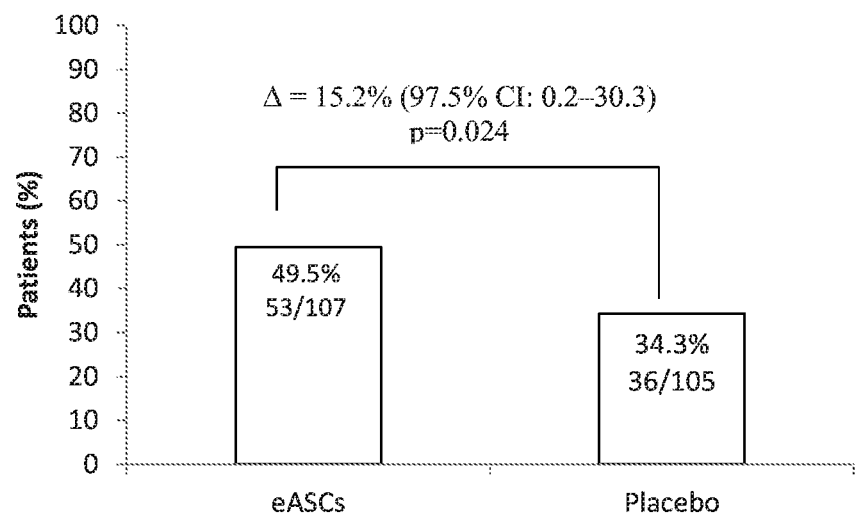
FIG. 3A-C: shows the Primary endpoint: Combined clinical and radiological remission* at week 24 in ITT population (FIG. 3A). Combined clinical and radiological remission* at week 24 in mITT population (FIG. 3B). Combined remission* by week 24 according to randomization stratification factors, i.e., Crohn's disease treatments being received at the time of randomization, in mITT population (FIG. 3C). Cx601, allogeneic, expanded, adipose-derived stem cells; IS, immunosuppressant; ITT, intention to treat; mITT, modified intention to treat; TNF, tumor necrosis factor. *Clinical assessment of closure of all treated external openings that were draining at baseline, and the absence of collections >2 cm of the treated perianal fistulas in ≥2 of 3 dimensions on centrally blinded MRI assessment by week 24. Clinical assessment of closure was defined as absence of draining despite gentle finger compression.
Figure 3B:
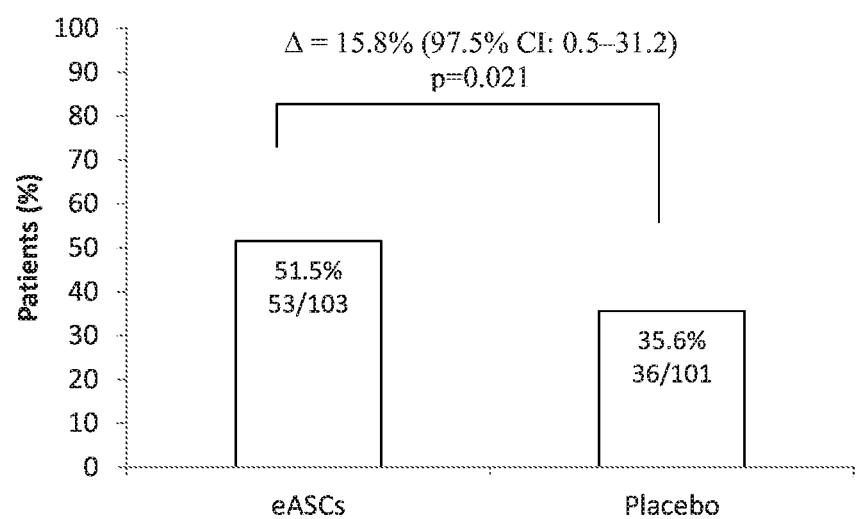
Figure 3C:
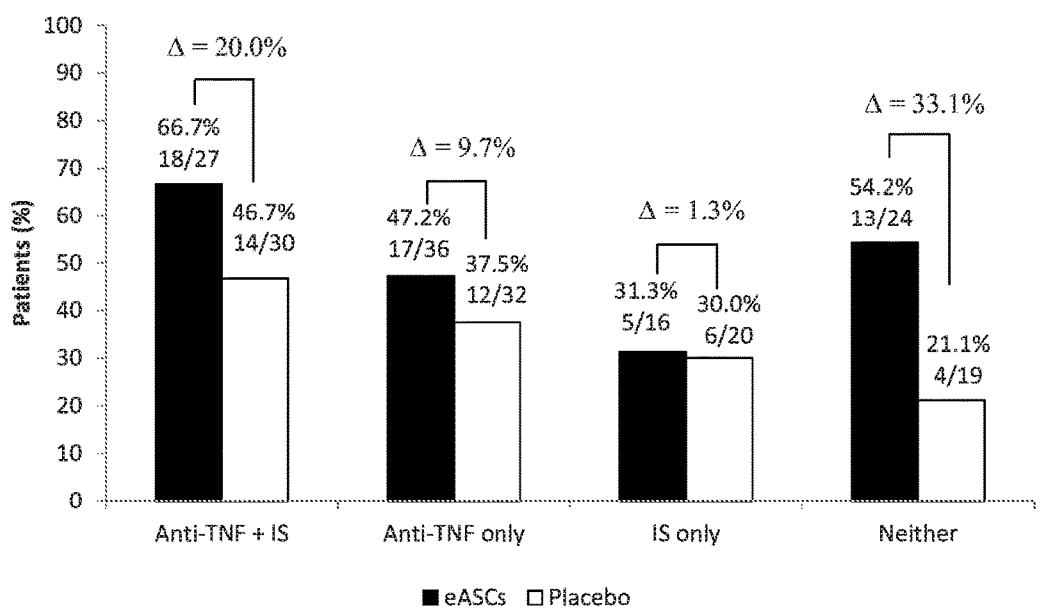

A significantly greater proportion of Cx601-treated patients achieved the primary endpoint of combined remission at week 24 vs placebo in the ITT (49.5% and 34.3%, respectively; difference [97.5% CI]: 15.2% [0.2-30.3]; p=0.0241) and the mITT populations (51.5% and 35.6%; 15.8% [0.5-31.2]; p=0.021; FIGS. 3A and B). These results were confirmed in the PP populations and in additional sensitivity analyses (Table 51). The effect of Cx601 was greater than placebo in the 4 randomization strata, with the numerically greatest effect of Cx601 being observed in patients receiving neither or both anti-TNF and immunosuppressant therapies at randomization (treatment difference 33.1% and 20.0%, respectively; FIG. 3C).

In the mITT population, a numerically greater proportion of patients in the Cx601 vs placebo group achieved clinical remission (55.3% and 42.6%, respectively; difference [95% CI]: 12.8% [−0.8-26.4]; p=0.057) and had a response (68.9% and 55.4%, respectively; 13.5% [0.3-26.7] p=0.045) by week 24.

The median time to clinical remission was around 2-fold shorter with Cx601 vs placebo (6.7 [95% CI, 6.4-11.9] weeks and 14.6 [11.9-22.9] weeks), as was the median time to response (6.3 [6.0-6.6] weeks and 11.7 [6.7-12.9] weeks).

The improvement in PDAI with Cx601 in the mITT population was significantly greater than with placebo at weeks 6 (change from baseline treatment difference [95% CI]: −1.0 [−1.7 to −0.3]), week 12 (−1.2 [−2.0 to −0.4]), and week 18 (−1.2 [−2.0 to −0.3]), but not at week 24 (−0.8 [−1.8 to 0.2]). For total and subdomain IBDQ and CDAI scores, there were no significant differences between treatment groups (Table S2).

Safety

The percentage of patients in the Cx601 and placebo groups who experienced TEAEs was similar (66.0% and 64.7%, respectively; Table 2). The most commonly reported TEAEs were proctalgia, anal abscess and nasopharyngitis. A higher proportion of patients in the placebo vs Cx601 group experienced treatment-related TEAEs (29.4% and 17.5%, respectively), the most common of which were anal abscess and proctalgia.

The majority of TEAEs were mild or moderate in intensity. Few patients withdrew from the study due to TEAEs (4.9% and 5.9%), whereas a slightly higher proportion of patients in the Cx601 group experienced serious TEAEs (17.5% and 13.7%). The most common serious TEAE was anal abscess (Cx601: 8.7%; placebo: 6.9%). There were no deaths.

Discussion and Overview

This is the first large-scale, randomized, placebo-controlled clinical study of the treatment of complex therapy-refractory perianal fistulas in patients with Crohn's disease. In the difficult-to-treat study population of patients who had complex perianal fistulas and had failed conventional or biologic therapy, 1 in 2 patients treated with Cx601 alone or added on to current medical therapy achieved combined clinical and radiological remission at week 24. This result was consistent across all statistical populations, despite patients in the Cx601 group having more multiple tract fistulas. The study results therefore show that Cx601 offers treatment-refractory patients a first real closure alternative for complex perianal fistulas to radical surgical approaches.

The primary endpoint of combined clinical and radiological remission is more stringent than that used in other randomized clinical studies of treatments for perianal fistulas in Crohn's disease, which have typically assessed clinical responses (i.e., ≥50% reduction in the number of draining fistulas) or clinical remission.[48,412] This is the first large-scale randomized clinical trial to use clinical assessment of fistula closure and MRI assessment of absence of abscesses as recommended in the European Crohn's and Colitis Organisation guidelines.[429]

The secondary efficacy analyses reinforce the clinical benefit of Cx601. With Cx601, the time to clinical remission and response was rapid, occurring in half of the time of that in the placebo group. The difference in clinical remission rates between Cx601 and placebo groups did not reach statistical significance due to a considerably higher "placebo" effect (42.6%) than expected and observed in previous studies (13-19%).[48,412,427] The placebo effects according to randomization strata (i.e., highest with concomitant anti-TNF and immunosuppressant [46.7%] and lowest with neither treatment [21.1%]) suggests that the higher placebo effect in this study may have been driven by concomitant medication use. Surgical drainage and internal orifice closure may also have increased the placebo response. Whereas beneficial improvements in PDAI scores were seen in the Cx601 group, there were no differences in IBDQ and CDAI scores between treatment groups. This was probably due to the low CDAI (an inclusion criterion) and high IBDQ at baseline.

The safety data show that Cx601 was well tolerated in the study population in agreement with the results of the prior phase ½a study.[423] Treatment-related TEAEs occurred more frequently in the placebo group and so may be related to the natural course of disease or surgical study procedures. The favorable safety profile may represent an advantage over anti-TNF therapies which are associated with several serious safety concerns resulting from immunogenicity to the drug and an increased risk of infections, including tuberculosis.[430,431]

The results of this study are encouraging, considering the need for effective and well tolerated new treatment options for patients with Crohn's disease and complex perianal fistulas. This study also has major implications for the care of Crohn's disease patients with treatment-refractory complex perianal fistulas, as many of them must currently undergo repeated surgery with the risk of damaging sphincteric muscles, resulting in fecal incontinence. As a result, 12-38% of patients with perianal fistulizing disease require proctectomy.[432] In contrast, the administration of Cx601 is minimally invasive and may be performed in an outpatient setting.

Limitations of this trial were the exclusion of patients with more than 2 internal and 3 external openings, as well as those with previous surgery other than drainage and seton placement. Furthermore, whether TEAEs were related to the surgical procedure was not established.

In conclusion, Cx601 is an effective and safe therapy for complex perianal fistulas in Crohn's disease that failed to respond to conventional and/or biologic treatments.

TABLE 1

Patient characteristics (safety population).

| Variable | Cx601 (N = 103) | Placebo (N = 102) |
|---|---|---|
| Age - yr | 38.9 (13.1) | 37.6 (13.2) |
| Male sex - no. (%) | 57 (55.3) | 54 (52.9) |
| Ethnicity - no. (%) | | |
| Caucasian | 96 (93.2) | 93 (91.2) |
| Black | 4 (3.9) | 1 (1.0) |
| Other | 0 | 1 (1.0) |
| Missing | 3 (2.9) | 7 (6.9) |
| Weight - kg | 73.3 (14.4) | 71.4 (15.0) |
| CD duration - yr | 11.8 (9.8) | 11.4 (9.0) |
| Prior CD medication in last 6 months - no. (%) | | |
| Antibiotics | 78 (75.7) | 72 (70.6) |
| Immunosuppressants | 87 (84.5) | 74 (72.5) |
| Anti-TNF | 80 (77.7) | 82 (80.4) |
| Concomitant CD medication (stratification factor) - no. (%) | | |
| Anti-TNF | 36 (35.0) | 32 (31.4) |
| Immunosuppressants | 16 (15.5) | 21 (20.6) |
| Anti-TNF + immunosuppressants | 27 (26.2) | 30 (29.4) |
| Neither | 24 (23.3) | 19 (18.6) |
| Perianal Crohn's Disease Activity Index* | 6.7 (2.5) | 6.5 (2.9) |
| Fistula openings - no. (%) | | |
| 0 internal + 1 external | 0 | 1 (1.0) |
| 1 internal + 1 external | 55 (53.4) | 70 (68.6) |
| 1 internal + 2 external | 23 (22.3) | 17 (16.7) |
| 1 internal + 3 external | 4 (3.9) | 3 (2.9) |
| 2 internal + 1 external | 3 (2.9) | 2 (2.0) |
| 2 internal + 2 external | 14 (13.6) | 8 (7.8) |
| 2 internal + 3 external | 4 (3.9) | 1 (1.0) |
| Crohn's Disease Activity Index† | 87.8 (48.3) | 92.5 (55.3) |
| Inflammatory Bowel Disease Questionnaire‡ | 173.5 (31.6) | 169.8 (36.2) |
| C reactive protein - mg/L | 7.9 (11.5) | 6.3 (9.5) |
| Hemoglobin - mmol/L | 8.3 (0.8) | 8.3 (0.8) |

CD, Crohn's disease;
Cx601, allogeneic, expanded, adipose-derived stem cells;
TNF, tumor necrosis factor.
Data are means (standard deviation) unless otherwise stated.
*Scores for Perianal Crohn's Disease Activity Index can range from 0 to 20; higher scores indicate more severe disease.
†Scores for Crohn's Disease Activity Index can range from 0 to 600; higher scores indicate more severe disease.
‡Scores for Inflammatory Bowel Disease Questionnaire can range from 32 to 224; higher scores indicate better quality of life.

TABLE 2

Treatment-emergent adverse events up to week 24 (safety population).

| TEAE - no. (%) | Cx601 (N = 103) | Placebo (N = 102) |
|---|---|---|
| Overall | 68 (66.0) | 66 (64.7) |
| TEAEs leading to study withdrawal | 5 (4.9) | 6 (5.9) |
| Serious TEAEs | 18 (17.5) | 14 (13.7) |
| TEAEs in ≥5.0% patients* | | |
| Proctalgia | 13 (12.6) | 11 (10.8) |
| Anal abscess | 12 (11.7) | 13 (12.7) |
| Nasopharyngitis | 10 (9.7) | 5 (4.9) |
| Diarrhea | 7 (6.8) | 3 (2.9) |
| Abdominal pain | 4 (3.9) | 6 (5.9) |
| Fistula | 3 (2.9) | 6 (5.9) |
| Treatment-related TEAEs | 18 (17.5) | 30 (29.4) |

TABLE 2-continued

Treatment-emergent adverse events up to week 24 (safety population).

| TEAE - no. (%) | Cx601 (N = 103) | Placebo (N = 102) |
|---|---|---|
| Treatment-related TEAEs in ≥2.0% patients* | | |
| Anal abscess | 6 (5.8) | 9 (8.8) |
| Proctalgia | 5 (4.9) | 9 (8.8) |
| Procedural pain | 1 (1.0) | 2 (2.0) |
| Fistula discharge | 1 (1.0) | 2 (2.0) |
| Induration | 0 | 2 (2.0) |

TEAE, treatment-emergent adverse event;
Cx601, allogeneic, expanded, adipose-derived stem cells;
*In either treatment group.

TABLE S1

Supportive and sensitivity analyses for primary endpoint: combined remission.*

| Type of analysis | Analysis set | Details of handling missing data | Cx601 (%) | Placebo (%) | Difference (%) (97.5% CI) | p-value |
|---|---|---|---|---|---|---|
| Supportive | ITT | Non-response/non-remission imputed for all missing data and after rescue therapy (no LOCF) | 48.6 | 32.4 | 16.2 (1.3-31.1) | 0.014 |
| Supportive | PP1† | LOCF applied Non-response/non-remission is imputed after rescue therapy | 57.0 | 36.9 | 20.1 (3.3-36.9) | 0.010 |
| Supportive | PP2‡ | Non-response/non-remission is imputed after rescue therapy | 63.2 | 39.7 | 23.4 (5.6-41.3) | 0.005 |
| Sensitivity | ITT | Missing = non-response/non-remission after LOCF applied. Rescue medication not considered as failure | 49.5 | 34.3 | 15.2 (0.2-30.3) | 0.024 |
| Sensitivity | ITT | Missing = non-response/non-remission after LOCF applied. Logistic analysis including stratification factor and number of baseline external openings as factors | 49.5 | 34.3 | NA | 0.017 |

CI, confidence interval;
Cx601, allogeneic, expanded, adipose-derived stem cells;
ITT, intention to treat;
LOCF, last observation carried forward;
NA, not applicable;
PP, per protocol;
TNF, tumor necrosis factor.
Rescue therapy is defined as corticoids at 40 mg prednisone equivalent for ≥12 weeks; new anti-TNF compared with baseline therapy for ≥8 weeks; new immunosuppressant compared with baseline therapy for ≥12 weeks; or surgical intervention for the treated fistula.
*Clinical assessment of closure of all treated external openings that were draining at baseline, and the absence of collections >2 cm of the treated perianal fistulas in ≥2 of 3 dimensions on centrally blinded MRI assessment by week 24. Clinical assessment of closure was defined as absence of draining despite gentle finger compression.
†PP1 population includes those without major protocol deviations (Cx601, n = 86; Placebo, n = 84).
‡PP2 population includes PP1 patients who completed the week 24 visit (Cx601, n = 76; Placebo, n = 73).

TABLE S2

Patient-reported outcomes from the Crohn's Disease Activity Index (CDAI)* and Inflammatory Bowel Disease Questionnaire (IBDQ)† scores up to week 24 (mITT population).

| | Cx601 (N = 103) | Placebo (N = 101) | Treatment difference (95% CI) |
|---|---|---|---|
| CDAI Total | | | |
| Baseline | 87.8 (48.3) | 93.3 (55.0) | |
| Week 24 | 92.5 (66.5) | 94.1 (76.1) | |
| Change from baseline | 5.7 (62.2) | 2.2 (65.5) | 1.8 (−16.0 to 19.7) |
| No. of liquid stools | | | |
| Baseline | 9.8 (12.3) | 9.3 (9.4) | |
| Week 24 | 9.5 (12.6) | 10.0 (12.6) | |
| Change from baseline | −0.0 (9.5) | 0.9 (10.7) | −0.7 (−3.4 to 2.1) |
| Abdominal pain | | | |
| Baseline | 1.6 (2.9) | 2.0 (3.1) | |
| Week 24 | 2.7 (4.5) | 3.0 (4.1) | |
| Change from baseline | 1.1 (4.4) | 0.9 (4.0) | −0.1 (−1.2 to 1.1) |
| General well being | | | |
| Baseline | 2.7 (3.7) | 3.2 (4.1) | |
| Week 24 | 3.1 (4.6) | 3.3 (4.7) | |
| Change from baseline | 0.6 (4.5) | 0.3 (4.5) | 0.1 (−1.1 to 1.3) |
| IBDQ Total | | | |
| Baseline | 173.5 (31.6) | 169.4 (36.1) | |
| Week 24 | 178.3 (34.6) | 174.7 (36.2) | |
| Change from baseline | 3.8 (25.5) | 4.0 (25.6) | 0.3 (−6.6 to 7.3) |
| Bowel function | | | |
| Baseline | 57.1 (9.2) | 56.6 (9.9) | |
| Week 24 | 57.2 (10.2) | 56.4 (9.8) | |
| Change from baseline | 0.0 (7.6) | −0.6 (8.2) | 0.5 (−1.6 to 2.7) |
| Emotional status | | | |
| Baseline | 62.9 (14.5) | 61.4 (15.2) | |
| Week 24 | 64.7 (15.6) | 63.9 (15.3) | |
| Change from baseline | 1.7 (11.3) | 2.1 (11.2) | −0.3 (−3.3 to 2.7) |
| Systemic symptoms | | | |
| Baseline | 25.8 (5.2) | 24.9 (6.5) | |
| Week 24 | 26.2 (5.9) | 25.6 (6.3) | |
| Change from baseline | 0.3 (4.7) | 0.6 (5.1) | −0.1 (−1.4 to 1.2) |
| Social function | | | |
| Baseline | 27.7 (6.9) | 26.5 (8.4) | |
| Week 24 | 29.5 (7.3) | 28.4 (8.0) | |
| Change from baseline | 1.6 (6.4) | 1.7 (6.0) | 0.3 (−1.3 to 2.0) |

CI, confidence interval;
Cx601, allogeneic, expanded, adipose-derived stem cells;
mITT, modified intention to treat.
Data are means (standard deviation).
*Scores for Crohn's Disease Activity Index (CDAI) can range from 0 to 600; higher scores indicate more severe disease.
†Scores for Inflammatory Bowel Disease Questionnaire (IBDQ) can range from 32 to 224; higher scores indicate better quality of life.

Embodiments of the invention include:
1. Expanded allogeneic adipose tissue-derived stromal stem cells for use in a method of treating a refractory complex perianal fistula in a patient having Crohn's disease.
2. Expanded allogeneic adipose tissue-derived stromal stem cells for use according to embodiment 1, wherein the fistula comprises one, two or all three of: multiple tracts, two internal openings and three external openings.
3. Expanded allogeneic adipose tissue-derived stromal stem cells for use according to embodiment 1 or embodiment 2, wherein the fistula is refractive to one or more of (i) antibiotic, (ii) immunosuppressant and (iii) anti-TNF therapy.
4. Expanded allogeneic adipose tissue-derived stromal stem cells for use according to any preceding embodiment, wherein the patient receives neither or both of an anti-TNF therapy and immunosuppressant therapy.
5. Expanded allogeneic adipose tissue-derived stromal stem cells for use according to any preceding embodiment, wherein the patient:
   (a) has non-active or mildly active Crohn's disease; and/or
   (b) luminal Crohn's disease.
6. Expanded allogeneic adipose tissue-derived stromal stem cells for use according to any preceding embodiment, wherein the cells are injected intralesionally.
7. Expanded allogeneic adipose tissue-derived stromal stem cells for use according to any preceding embodiment, wherein 120 million cells are administered in a single administration.
8. Expanded allogeneic adipose tissue-derived stromal stem cells for use according to any preceding embodiment, wherein the therapy induces combined remission or clinical remission.
9. Expanded allogeneic adipose tissue-derived stromal stem cells for use according to embodiment 8, wherein the combined remission or clinical remission is achieved within 24 weeks, within 18 weeks or within 12 weeks.
10. Expanded allogeneic adipose tissue-derived stromal stem cells for use according to embodiment 9, wherein the combined remission or clinical remission is achieved within 8 weeks or within 6 weeks.
11. Expanded allogeneic adipose tissue-derived stromal stem cells for use according to any preceding embodiment, wherein the fistula is monitored by MRI.
12. Expanded allogeneic adipose tissue-derived stromal stem cells for use according to any preceding embodiment, wherein at least about 90% or at least about 95% of the expanded allogeneic adipose tissue-derived stromal stem cells express the surface markers HLA I, CD29, CD44, CD59, CD73, CD90, and CD105.
13. Expanded allogeneic adipose tissue-derived stromal stem cells for use according to any preceding embodiment, wherein fewer than about 5% of the expanded allogeneic adipose tissue-derived stromal stem cells express the surface markers HLAII, CD11b, CD11c, CD14, CD45, CD31, CD34, CD80 and CD86.
14. Use of expanded allogeneic adipose tissue-derived stromal stem cells in the manufacture of a medicament for treating a refractory complex perianal fistula in a patient having Crohn's disease.
15. A method of treating a refractory complex perianal fistula in a patient having Crohn's disease, in a patient in need of such treatment, comprising the step of administering expanded allogeneic adipose tissue-derived stromal stem cells to the fistula.

16. A use according to embodiment 14 or a method according to embodiment 15, further comprising the features of any of embodiments 2 to 13.

REFERENCES

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

1. American Gastroenterological Association Medical Position Statement: Perianal Crohn's Disease. *Gastroenterology* (2003) 125:1503-1507.
2. Levy C, Tremaine W J. *Inflamm Bowel Dis* (2002) 8(2):106-11.
3. Pennincke F, D'Hoore A, Filez L. *Acta Gastroenterol Belg* (2001) 64(2):223-226.
4. Rius J, Nessim A, Nogueras J J, Wexner S D. *Eur J Surg* (2000) 166(3):218-222.
5. Mizuno H, Zuk P A, Zhu M, Lorenz H P, Benhaim P, Hedrick M H. *Plastic Reconstr Surg* (2002) 109(1): 199-209.
6. Zuk P A, Zhu M, Mizuno H, et al. *Tissue Eng* (2001) 7(2): 211-228.
7. Garcia-Olmo D, Garcia-Arranz M, Gomez-Garcia L et al. *Int J Colorectal Dis* (2003) 18: 451-454.
8. Abkowitz J L. *New Engl J Med* (2002) 346(10): 770-772.
9. Matsubara H. *Lancet* (2004) 363:746-747.
10. Cowan C M, Shi Y Y, Aalami 00, et al. *Nat Biotechnol.* (2004) 22(5):560-7
11. Garcia-Olmo D, Garcia-Olmo M A. *New Eng J Med* (2003) 349: 1480-1481.
12. Osawa M., Hanada K., Hanada H. and Nakauchi H. (1996) *Science* 273, 242-245.
13. Morrison S. J., Uchida N. and Weissman I L (1995) *Annu. Rev. Cell Dev. Biol.* 11, 35-71.
14. Ivanova N. B., Dimos J. T., Schaniel C., Hackney J. A., Moore K. A., Lemischka* I. R. (2002) *Science* 298, 601-604.
15. Phillips R L. (2000) *Curr Top Microbiol Immunol.* 251, 13-19.
16. Ramalho-Santos M, Yoon S, Matsuzaki Y, Mulligan R C, Melton D A. (2002) *Science* 298, 597-600.
17. De Ugarte D A, Morizono K, Elbarbary, AAlfonso Z, Zuk P A, Zhu M, Dragoo J L, Ashjian P, Thomas B, Benhaim P, Chen I, Fraser J, Hedrick M H. (2003) *Cells Tissues Organs* 174 (3), 101-109.
18. Friedenstein A J, Gorskaja J F, Kulagina N N, *Exp Hematol.* (1976) September; 4(5):267-74.
19. Caplan A I *J Orthop Res*. (1991) September; 9(5):641-50
20. Pittenger, M. F. et al. (1999) *Science* 284: 143-147
21. Beresford J N, Bennett J H, Devlin C, Leboy P S, Owen M E, *J Cell Sci*. (1992) June; 102 (Pt 2):341-51
22. Yoo J U, Johnstone B, *Clin Orthop*. (1998) October; (355 Suppl):S73-81
23. Wakitani S. et al. (1995) *Muscle Nerve* 18: 1417-1426.
24. Haynesworth S E, Goshima J, Goldberg V M, Caplan A I, *Bone.* 1992; 13(1):81-8.
25. Sanchez-Ramos J, Song S, Cardozo-Pelaez F, Hazzi C, Stedeford T, Willing A, Freeman T B, Saporta S, Janssen W, Patel N, Cooper D R, Sanberg P R, *Exp Neurol*. (2000) August; 164(2):247-56.
26. Rogers J J, Young H E, Adkison L R, Lucas P A, Black A C Jr, Am Surg. (1995) March; 61(3):231-6.
27. Jiang Y, Vaessen B, Lenvik T, Blackstad M, Reyes M, Verfaillie C M, *Exp Hematol*. (2002) August; 30(8):896-904.
28. Caplan A I, Bruder S P, *Trends Mol Med.* (2001) June; 7(6):259-64.
29. Stanford, C. M. et al. (1995) *J Biol Chem* 270: 9420-9428.

"A" References

A1. Baumgart D C, Sandborn W J. Crohn's disease. Lancet 2012; 380:1590-605.
A2. Schwartz D A, Loftus E V, Jr., Tremaine W J, et al. The natural history of fistulizing Crohn's disease in Olmsted County, Minn. Gastroenterology 2002; 122:875-80.
A3. Eglinton T W, Barclay M L, Gearry R B, Frizelle F A. The spectrum of perianal Crohn's disease in a population-based cohort. Dis Colon Rectum 2012; 55:773-7.
A4. Hellers G, Bergstrand O, Ewerth S, Holmstrom B. Occurrence and outcome after primary treatment of anal fistulae in Crohn's disease. Gut 1980; 21:525-7.
A5. Scharl M, Rogler G. Pathophysiology of fistula formation in Crohn's disease. World J Gastrointest Pathophysiol 2014; 5:205-12.
A6. Nielsen O H, Rogler G, Hahnloser D, Thomsen O O. Diagnosis and management of fistulizing Crohn's disease. Nat Clin Pract Gastroenterol Hepatol 2009; 6:92-106.
A7. Bell S J, Williams A B, Wiesel P, Wilkinson K, Cohen R C, Kamm M A. The clinical course of fistulating Crohn's disease. Aliment Pharmacol Ther 2003; 17:1145-51.
A8. Sands B E, Anderson F H, Bernstein C N, et al. Infliximab maintenance therapy for fistulizing Crohn's disease. N Engl J Med 2004; 350:876-85.
A9. Thia K T, Mahadevan U, Feagan B G, et al. Ciprofloxacin or metronidazole for the treatment of perianal fistulas in patients with Crohn's disease: a randomized, double-blind, placebo-controlled pilot study. Inflamm Bowel Dis 2009; 15:17-24.
A10. Present D H, Korelitz B I, Wisch N, Glass J L, Sachar D B, Pasternack B S. Treatment of Crohn's disease with 6-mercaptopurine. A long-term, randomized, double-blind study. N Engl J Med 1980; 302:981-7.
A11. Pearson D C, May G R, Fick G H, Sutherland L R. Azathioprine and 6-mercaptopurine in Crohn disease. A meta-analysis. Ann Intern Med 1995; 123:132-42.
A12. Present D H, Rutgeerts P, Targan S, et al. Infliximab for the treatment of fistulas in patients with Crohn's disease. N Engl J Med 1999; 340:1398-405.
A13. Domenech E, Hinojosa J, Nos P, et al. Clinical evolution of luminal and perianal Crohn's disease after inducing remission with infliximab: how long should patients be treated? Aliment Pharmacol Ther 2005; 22:1107-13.
A14. Goldstein E S, Marion J F, Present D H. 6-Mercaptopurine is effective in Crohn's disease without concomitant steroids. Inflamm Bowel Dis 2004; 10:79-84.
A15. Korelitz B I, Present D H. Favorable effect of 6-mercaptopurine on fistulae of Crohn's disease. Dig Dis Sci 1985; 30:58-64.
A16. Brandt L J, Bernstein L H, Boley S J, Frank M S. Metronidazole therapy for perineal Crohn's disease: a follow-up study. Gastroenterology 1982; 83:383-7.
A17. Solomon M J, McLeod R S, O'Connor B I, Steinhart A J, et al. Combination ciprofloxacin and metronidazole in severe perianal Crohn's disease. Can J Gastroenterol 1993; 7:571-3.
A18. Molendijk I, Nuij V J, van der Meulen-de Jong A E, van der Woude C J. Disappointing durable remission rates in complex Crohn's disease fistula. Inflamm Bowel Dis 2014; 20:2022-8.
A19. Gecse K, Khanna R, Stoker J, et al. Fistulizing Crohn's disease: Diagnosis and management. United European Gastroenterol J 2013; 1:206-13.
A20. Singer N G, Caplan A I. Mesenchymal stem cells: mechanisms of inflammation. Annu Rev Pathol 2011; 6:457-78.
A21. DelaRosa O, Dalemans W, Lombardo E. Mesenchymal stem cells as therapeutic agents of inflammatory and autoimmune diseases. Curr Opin Biotechnol 2012; 23:978-83.
A22. Garcia-Olmo D, Guadalajara H, Rubio-Perez I, Herreros M D, De La Quintana P, Garcia-Arranz M. Recurrent anal fistulae: limited surgery supported by stem cells. World J Gastroenterol 2015; 21:3330-6.
A23. de la Portilla F, Alba F, Garcia-Olmo D, Herrerias J M, Gonzalez F X, Galindo A. Expanded allogeneic adipose-derived stem cells (eASCs) for the treatment of complex perianal fistula in Crohn's disease: results from a multicenter phase I/IIa clinical trial. Int J Colorectal Dis 2013; 28:313-23.
A24. Best W R, Becktel J M, Singleton J W, Kern F, Jr. Development of a Crohn's disease activity index. National Cooperative Crohn's Disease Study. Gastroenterology 1976; 70:439-44.
A25. Irvine E J. Usual therapy improves perianal Crohn's disease as measured by a new disease activity index. McMaster IBD Study Group. J Clin Gastroenterol 1995; 20:27-32.
A26. Guyatt G, Mitchell A, Irvine E J, et al. A new measure of health status for clinical trials in inflammatory bowel disease. Gastroenterology 1989; 96:804-10.
A27. Colombel J F, Schwartz D A, Sandborn W J, et al. Adalimumab for the treatment of fistulas in patients with Crohn's disease. Gut 2009; 58:940-8.
A28. Hochberg Y. A sharper Bonferroni procedure for multiple tests of significance. Biometrica 1988; 75:800-2.
A29. Van Assche G, Dignass A, Reinisch W, et al. The second European evidence-based Consensus on the diagnosis and management of Crohn's disease: Special situations. J Crohns Colitis 2010; 4:63-101.
A30. Schwartz D A, Herdman C R. Review article: The medical treatment of Crohn's perianal fistulas. Aliment Pharmacol Ther 2004; 19:953-67.
A31. American Gastroenterological Association medical position statement: perianal Crohn's disease. Gastroenterology 2003; 125:1503-7.
A32. Geltzeiler C B, Wieghard N, Tsikitis V L. Recent developments in the surgical management of perianal fistula for Crohn's disease. Ann Gastroenterol 2014; 27:320-30.

EQUIVALENTS

The present invention provides, among other things, methods and compositions for treating and preventing fistula. While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

We claim:
1. A method of treating a refractory complex perianal fistula in a subject having Crohn's disease comprising administering a therapeutic amount of a population of expanded allogeneic adipose tissue-derived stromal stem cells to the subject, wherein:
    (i) the fistula comprises multiple tracts;
    (ii) a fixed dose of about 120 million expanded allogeneic adipose tissue-derived stromal stem cells is administered to the subject in a single procedure, wherein each fistula tract receives at least a proportion of this dose and wherein approximately half of the dose is injected into the tissue surrounding the internal opening or openings and the other half is injected into the fistula walls all along the fistula tracts; and
    (iii) the administration of the therapeutic amount of the population of expanded allogeneic adipose tissue-derived stromal stem cells induces combined remission within 24 weeks that is statistically superior to placebo.
2. The method according to claim 1, wherein the fistula comprises 2 internal openings.
3. The method according to claim 1, wherein the fistula comprises 2 or 3 external openings.
4. The method according to claim 1, wherein the administering a therapeutic amount of a population of expanded allogeneic adipose tissue-derived stromal stem cells to the subject induces clinical remission within 6 weeks.
5. The method according to claim 1, wherein the administering a therapeutic amount of a population of expanded allogeneic adipose tissue-derived stromal stem cells induces combined remission within 18 weeks that is statistically superior to placebo.
6. The method according to claim 1, wherein an improvement in perianal disease activity index (PDAI) is achieved within 24 weeks.
7. The method according to claim 6, wherein the improvement in PDAI is an improvement of greater than 1.5 PDAI points.

8. The method according to claim 6, wherein the improvement in PDAI is an improvement of at least two PDAI points.

9. The method according to claim 1, wherein the fistula is refractive to (i) antibiotic, (ii) immunosuppressant, (iii) anti-TNF therapy, or (iv) any combination thereof.

10. The method according to claim 1, wherein the subject receives neither or both of an anti-TNF therapy and immunosuppressant therapy.

11. The method according to claim 1, wherein the subject has:
   (a) non-active or mildly active Crohn's disease;
   (b) luminal Crohn's disease; or
   (c) both (a) and (b).

12. The method according to claim 1, wherein the fistula is monitored by magnetic resonance imaging (MRI).

13. The method according to claim 1, wherein the expanded allogeneic adipose tissue-derived stromal stem cells express four or more of HLAI, CD29, CD44, CD59, CD73, CD90, and CD105; and do not express four or more of HLAII, CD11b, CD11c, CD14, CD45, CD31, CD34, and CD80.

14. The method according to claim 1, wherein the administering a therapeutic amount of a population of expanded allogeneic adipose tissue-derived stromal stem cells to the subject induces clinical remission within 8 weeks.

15. The method according to claim 14, wherein the clinical remission is sustained through to 24 weeks from the administering a therapeutic amount of a population of expanded allogeneic adipose tissue-derived stromal stem cells to the subject.

16. The method according to claim 1, wherein the administering a therapeutic amount of a population of expanded allogeneic adipose tissue-derived stromal stem cells induces combined remission within 12 weeks that is statistically superior to placebo.

17. The method according to claim 1, wherein the administering a therapeutic amount of a population of expanded allogeneic adipose tissue-derived stromal stem cells induces combined remission within 10 weeks that is statistically superior to placebo.

18. The method according to claim 1, wherein an improvement in perianal disease activity index (PDAI) is achieved within 18 weeks.

19. The method according to claim 1, wherein an improvement in perianal disease activity index (PDAI) is achieved within 12 weeks.

20. The method according to claim 1, wherein an improvement in perianal disease activity index (PDAI) is achieved within 10 weeks.

* * * * *